US007662395B2

(12) United States Patent
Schlom et al.

(10) Patent No.: US 7,662,395 B2
(45) Date of Patent: *Feb. 16, 2010

(54) METHOD OF ENHANCING A TARGETED IMMUNE RESPONSE AGAINST TUMORS

(75) Inventors: Jeffrey Schlom, Potomac, MD (US); Judith Kantor, Rockville, MD (US); James W. Hodge, Gaithersburg, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/112,819

(22) Filed: Apr. 30, 2008

(65) Prior Publication Data
US 2008/0279887 A1 Nov. 13, 2008

Related U.S. Application Data

(60) Division of application No. 11/090,686, filed on Mar. 28, 2005, now Pat. No. 7,368,116, which is a continuation of application No. 10/341,431, filed on Jan. 14, 2003, now Pat. No. 6,893,869, which is a division of application No. 09/480,340, filed on Jan. 7, 2000, now Pat. No. 6,548,068, which is a continuation of application No. 08/483,316, filed on Jun. 7, 1995, now Pat. No. 6,045,802, which is a continuation-in-part of application No. 08/317,268, filed on Oct. 3, 1994, now abandoned.

(51) Int. Cl.
*A61K 39/12* (2006.01)
(52) U.S. Cl. .................. 424/199.1; 435/320.1
(58) Field of Classification Search .............. 424/199.1, 424/232.1, 204.1
See application file for complete search history.

(56) References Cited

U.S. PATENT DOCUMENTS

| 4,690,915 | A | | 9/1987 | Rosenberg |
| 5,126,132 | A | | 6/1992 | Rosenberg |
| 5,206,353 | A | | 4/1993 | Berger et al. |
| 5,738,852 | A | | 4/1998 | Robinson et al. |
| 5,833,975 | A | | 11/1998 | Paoletti et al. |
| 6,045,802 | A | * | 4/2000 | Schlom et al. ............ 424/199.1 |
| 7,211,432 | B2 | | 5/2007 | Schlom et al. |
| 2004/0091995 | A1 | | 5/2004 | Schlom et al. |

FOREIGN PATENT DOCUMENTS

| WO | WO 91/02805 A2 | 3/1991 |
| WO | WO 92/19266 A1 | 11/1992 |
| WO | WO 92/20356 A1 | 11/1992 |
| WO | WO 94/16716 A1 | 8/1994 |
| WO | WO 94/24267 A1 | 10/1994 |
| WO | WO 95/09241 | * 4/1995 |

OTHER PUBLICATIONS

Anichini et al., "Melanoma cells and normal melanocytes share antigens recognized by HLA-A2-restricted cytotoxic T cell clones from melanoma patients," *J. Exp. Med.*, 177 (4), 989-998 (1993).
Arlen et al., "A novel ELISPOT assay to enhance detection of antigen-specific T cells employing antigen-presenting cells expressing vector-driven human B7-1," *J. Immunol. Methods*, 279 (1-2), 183-192 (2003).
Azuma et al., "B70 antigen is a second ligand for CTLA-4 and CD28," *Nature*, 366 (6450), 76-79 (1993).
Balloul et al., "Recombinant MUC 1 vaccinia virus: a potential vector for immunotherapy of breast cancer," *Cell. Mol. Biol.*, 40 (Suppl. 1), 49-59 (1994).
Bei et al., "Enhanced immune responses and anti-tumor activity by baculovirus recombinant carcinoembryonic antigen (CEA) in mice primed with the recombinant vaccinia CEA," *J. Immunother.*, 16 (4), 275-282 (1994).
Bei et al., "Serological and biochemical characterization of recombinant baculovirus carcinoembryonic antigen," *Mol. Immunol.*, 31 (10), 771-780 (1994).
Brichard et al., "The tyrosinase gene codes for an antigen recognized by autologous cytolytic T lymphocytes on HLA-A2 melanomas," *J. Exp. Med.*, 178 (2), 489-495 (1993).
Bronte et al., "IL-2 enhances the function of recombinant poxvirus-based vaccines in the treatment of established pulmonary metastases," *J. Immunol.*, 154 (10), 5282-5292 (1995).
Chen et al., "Tumor immunogenicity determines the effect of B7 costimulation on T cell-mediated tumor immunity," *J. Exp. Med.*, 179 (2), 523-532 (1994).
Chen et al., "Costimulation of antitumor immunity by the B7 counter-receptor for the T lymphocyte molecules CD28 and CTLA-4," *Cell*, 71 (7), 1093-1102 (1992).
Chen et al., "Costimulation of T cells for tumor immunity," *Immunol. Today*, 14 (10), 483-486 (1993).
Cochran et al., "In vitro mutagenesis of the promoter region for a vaccinia virus gene: evidence for tandem early and late regulatory signals," *J. Virol.*, 54 (1), 30-37 (1985).

(Continued)

*Primary Examiner*—Ali R. Salimi
(74) *Attorney, Agent, or Firm*—Leydig, Voit & Mayer, Ltd.

(57) ABSTRACT

The present invention is a composition of recombinant virus which has incorporated into its genome or portion thereof a gene encoding an antigen to a disease causing agent and a recombinant virus which has incorporated into its genome or portion thereof a gene encoding an immunostimulatory molecule(s) for the purpose of stimulating an immune response against the disease causing agent. Methods of treatment of diseases such as cancer and diseases caused by pathogenic microorganisms is provide using the composition.

8 Claims, 14 Drawing Sheets

OTHER PUBLICATIONS

"Current Protocols in Molecular Bioloav. Generation of Recombinant Vaccinia Viruses," 2, 16.17.1-6.17.16 (1994).
Döhring et al., "T-helper- and accessory-cell-independent cytotoxic responses to human tumor cells transfected with a B7 retroviral vector," *Int J. Cancer*, 57 (5), 754-759 (1994).
D'Urso et al., "Lack of HLA class I antigen expression by cultured melanoma cells FO-1 due to a defect in B2m gene expression," *J. Clin. Invest.*, 87(1), 284-292 (1991).
"Expression of Proteins in Mammalian Cells Using Vaccinia Viral Vectors, Overview of the Vaccinia Virus Expression System," *Current Protocols in Mol. Bio., Sect. IV*, Unit 16.15-16.19.9 (1991).
Flexner et al., "Expression of Human Interleukin-2 by Live Recombinant Virus," *Vaccines*, 87, 380-383 (1987).
Freeman et al., "B7.1, a new member of the Ig superfamily with unique expression on activated and neoplastic B cells," *J. Immunol.*, 143 (8), 2714-2722 (1989).
Freeman et al., "Cloning of B7-2: a CTLA-4 counter-receptor that costimulates human T cell proliferation," *Science*, 262 (5135), 909-911(1993).
Freeman et al., "Uncovering of functional alternative CTLA-4 counter-receptor in B7-deficient mice," *Science*, 262 (5135), 907-909 (1993).
Freeman et al., "Structure, expression, and T cell costimulatory activity of the murine homologue of the human B lymphocyte activation antigen B7," *J. Exp. Med.*, 174 (3), 625-631 (1991).
Gaugler et al., "Human gene MAGE-3 codes for an antigen recognized on a melanoma by autologous cytolytic T lymphocytes," *J. Exp. Med.*, 179 (3), 921-930 (1994).
Hathcock et al., "Comparative analysis of B7-1 and B7-2 costimulatory ligands: expression and function," *J. Exp. Med.*, 180 (2), 631-640 (1994).
Hazama et al., "Adjuvant-independent enhanced immune responses to recombinant herpes simlex virus type 1 glycoprotein D by fusion with biologically active interleukin-2," *Vaccine*, 11(6), 629-636 (1993).
Hellstrom et al., "On the role of costimulation in tumor immunity," *Ann. N. Y. Acad. Sci.*, 690, 225-231 (1993).
Hellstrom et al., "Tumor immunology: an overview," *Ann. N. Y. Acad. Sci.*, 690, 24-31 (1993).
Hinuma et al., "A novel strategy for converting recombinant viral protein into high immunogenic antigen," *FEBS Lett.*, 288 (1-2), 138-142 (1991).
Hodge et al., "Induction of antitumor immunity by recombinant vaccinia viruses expressing B7-1 or B7-2 costimulatory molecules," *Cancer Res.*, 54 (21), 5552-5555 (1994).
Hodge et al., "Admixture of a recombinant vaccinia virus containing the gene for the costimulatory molecule B7 and a recombinant vaccinia virus containing a tumor-associated antigen gene results in enhanced specific T-cell responses and antitumor immunity," *Cancer Res.*, 55(16), 3598-3603 (1995).
June et al., "The B7 and CD28 receptor families," *Immunol Today*, 15 (7), 321-331 (1994).
Kantor et al., "Antitumor activity and immune responses induced by a recombinant carcinoembryonic antigen-vaccinia virus vaccine," *J. Natl. Cancer Inst.*, 84 (14), 1084-1091 (1992).
Kantor et al., "Immunogenicity and safety of a recombinant vaccinia virus vaccine expressing the carcinoembryonic antigen gene in a nonhuman primate," *Cancer Res.*, 52 (24), 6917-6925 (1992).
Karupiah et al., "Recombinant vaccine vector-induced protection of athymic, nude mice from influenza A virus infection. Analysis of protective mechanisms," *Scand. J. Immunol.*, 36 (1), 99-105 (1992).
Kaufman et al., "A recombinant vaccinia virus expressing human carcinoembryonic antigen (CEA)," *Int. J. Cancer.*, 48(6), 900-907 (1991).
Kawakami et al., "Cloning of the gene coding for a shared human melanoma antigen recognized by autologous T cells infiltrating into tumor," *PNAS*, 91 (9), 3515-3519 (1994).
Kawakami et al., "Identification of the immunodominant peptides of the MART-1 human melanoma antigen recognized by the majority of HLA-A2-restricted tumor infiltrating lymphocytes," *J. Exp. Med.*, 180 (1), 347-352 (1994).
Kawakami et al., "Identification of a human melanoma antigen recognized by tumor-infiltrating lymphocytes associated with in vivo tumor rejection," *PNAS*, 91(14), 6458-6462 (1994).
Li et al., "Costimulation of tumor-reactive CD4+ and CD8+ T lymphocytes by B7, a natural ligand for CD28, can be used to treat established mouse melanoma," *J. Immunol.*, 53 (1), 421-428 (1994).
Lindley et al., "Construction and characterization of adenovirus coexpressing hepatitis B virus surface antigen and interleukin-6," *Gene*, 138 (1-2), 165-170 (1994).
Marincola et al., "Loss of HLA haplotype and B locus down-regulation in melanoma cell lines," *J. Immunol.*, 153 (3), 1225-1237 (1994).
Minev et al., "Insertion signal sequence fused to minimal peptides elicits specific CD8+ T-cell responses and prolongs survival of thymoma-bearing mice," *Cancer Res.*, 54 (15), 4155-4161 (1994).
Ochalek et al., "In vitro generation of therapeutic noncytolytic T-cells by soluble polyoma TAA and II-2," *Anticancer Res.*, 13(4), 1171-1177 (1993).
Ramsay et al., "Enhancement of mucosal IgA responses by interleukins 5 and 6 encoded in recombinant vaccine vectors," *Reprod. Fertil. Dev.*, 6 (3), 389-392 (1994).
Ramshaw et al., "Cytokine expression by recombinant viruses—a new vaccine strategy," *Trends Biotechnol.*, 10 (12), 424-426 (1992).
Restifo et al., "Defective presentation of endogenous antigens by a murine sarcoma. Implications for the failure of an anti-tumor immune response," *J. Immunol.*, 147 (4), 1453-1459 (1991).
Restifo et al., "Identification of human cancers deficient in antigen processing," *J. Exp. Med.*, 177 (2), 265-272 (1993).
Restifo et al., "Molecular mechanisms used by tumors to escape immune recognition: imnnunogenetherapy and the cell biology of major histocompatibility complex class I," *J. Immunother. Emphasis Tumor Immunol.*, 14(3), 182-190 (1993).
Rosenberg et al., "Experience with the use of high-dose interleukin-2 in the treatment of 652 cancer patients," *Ann. Surg.*, 210 (4), 474-485 (1989).
Rosenberg et al., "Treatment of 283 consecutive patients with metastatic melanoma or renal cell cancer using high-dose bolus interleukin 2," *JAMA*, 271 (12), 907-913 (1994).
Ruby et al., "Response of monkeys to vaccination with recombinant vaccinia virus which coexpress HIV gp160 and human interleukin-2," *Immunol. Cell Biol.*, 68, 113-117 (1990).
Schlom et al., "Recombinant Vaccines for the Active Specific Immunotheraphy of Human Cancer," *AIDS Res. Hum. Retrovir.*, 10 (Suppl. 1), S58 (1994).
Schwartz, "Costimulation of T lymphocytes: the role of CD28, CTLA-4, and B7/BB1 in interleukin-2 production and immunotherapy," *Cell*, 71 (7), 1065-1068 (1992).
Sivanandham et al., "Therapeutic effect of a vaccinia colon oncolysate prepared with interleukin-2-gene encoded vaccinia virus studied in a syngeneic CC-36 murine colon hepatic metastasis model," *Cancer Immunol. Immunother.*, 38 (4), 259-264 (1994).
Smith et al., "Vaccinia Virus Expression Vectors: Construction Properties and Applications," *Biotechniques*, 306-312 (1994).
Tanaka et al., "Immunotherapy of a vaccinia colon oncolysate prepared with interleukin-2 gene-encoded vaccinia virus and interferon-alpha increases the survival of mice bearing syngeneic colon adenocarcinoma," *J. Immunother. Emphasis Tumor Immunol.*, 16 (4), 283-293 (1994).
Taniguchi et al., "Structure and expression of a cloned cDNA for human interleukin-2," *Nature*, 302 (5906), 305-310 (1983).
Tartaglia et al., "Poxvirus-based vectors as vaccine candidates," *Crit. Rev. Immunol.*, 10(1), 13-30 (1990).
Townsend et al., "Tumor rejection after direct costimulation of CD8+ T cells by B7-transfected melanoma cells," *Science*, 259 (5093), 368-370 (1993).
Tsang et al., "The infection of human dendritic cells with recombinant avipox vectors expressing a costimulatory molecule transgene (CD80) to enhance the activation of antigen-specific cytolytic T cells," *Cancer Res.*, 61 (20), 7568-7576 (2001).
Kass et al., *Cancer Research*, 61: 206-214 (2001).
Kaufman et al., *J. Translational Med.*, 5: 60 (2007).

* cited by examiner

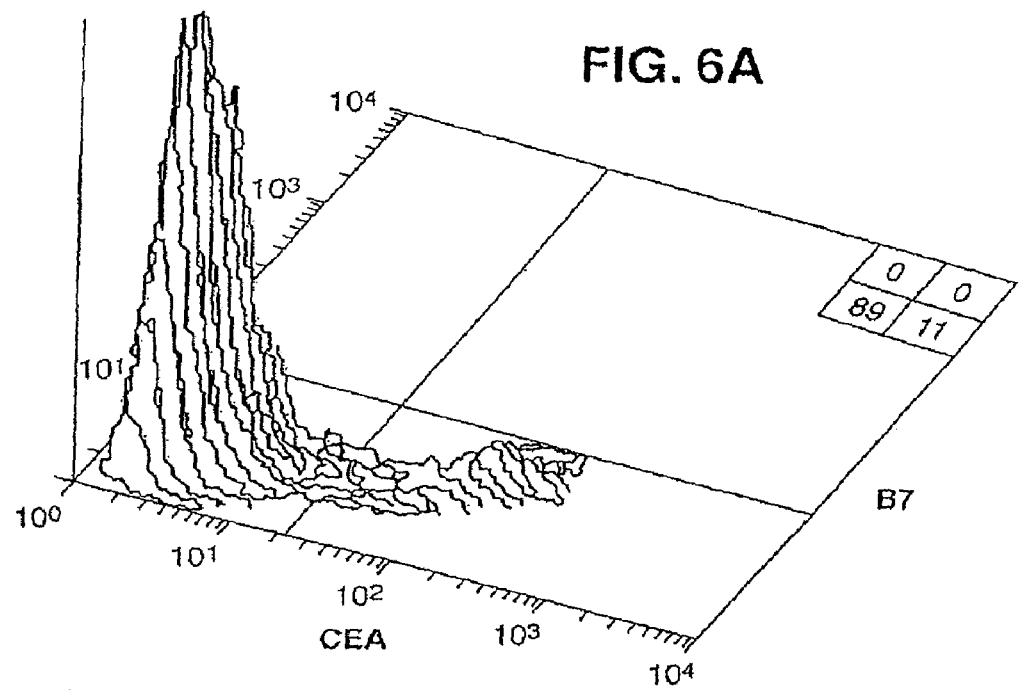
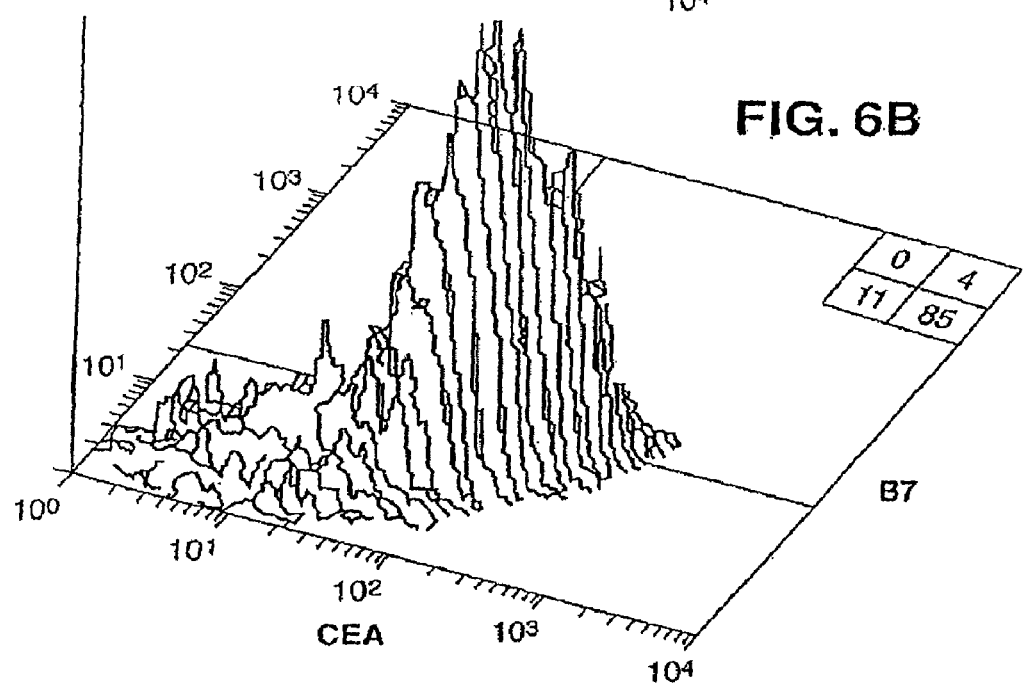

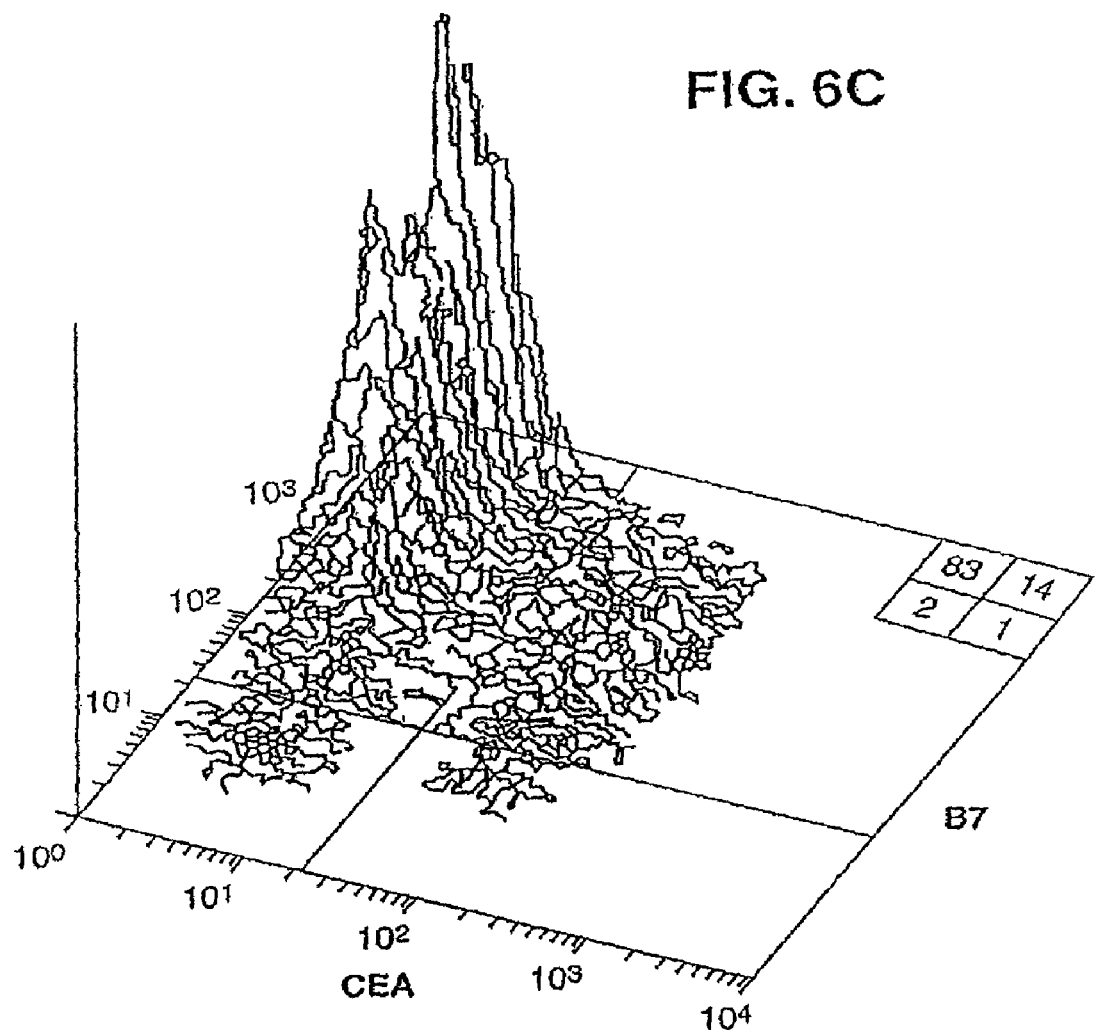

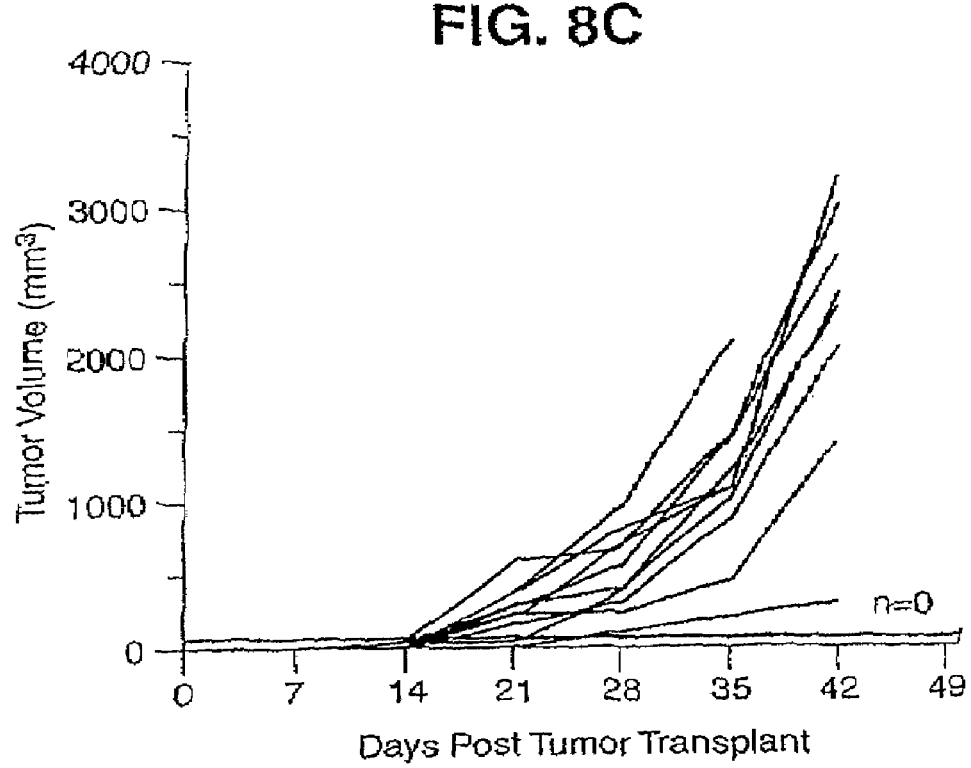
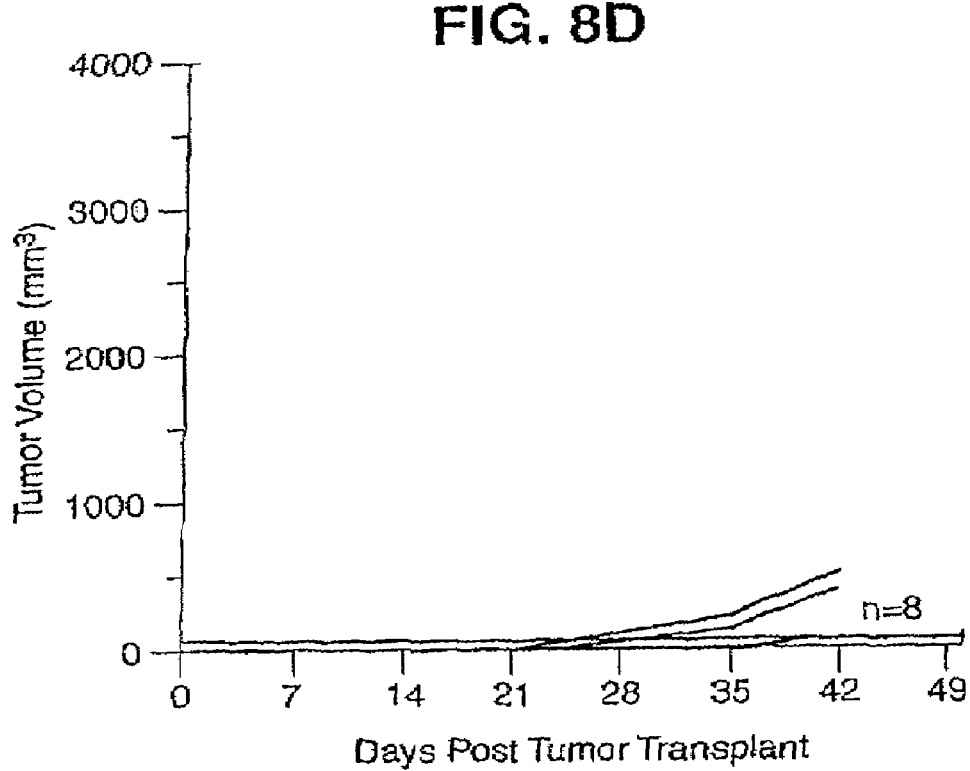

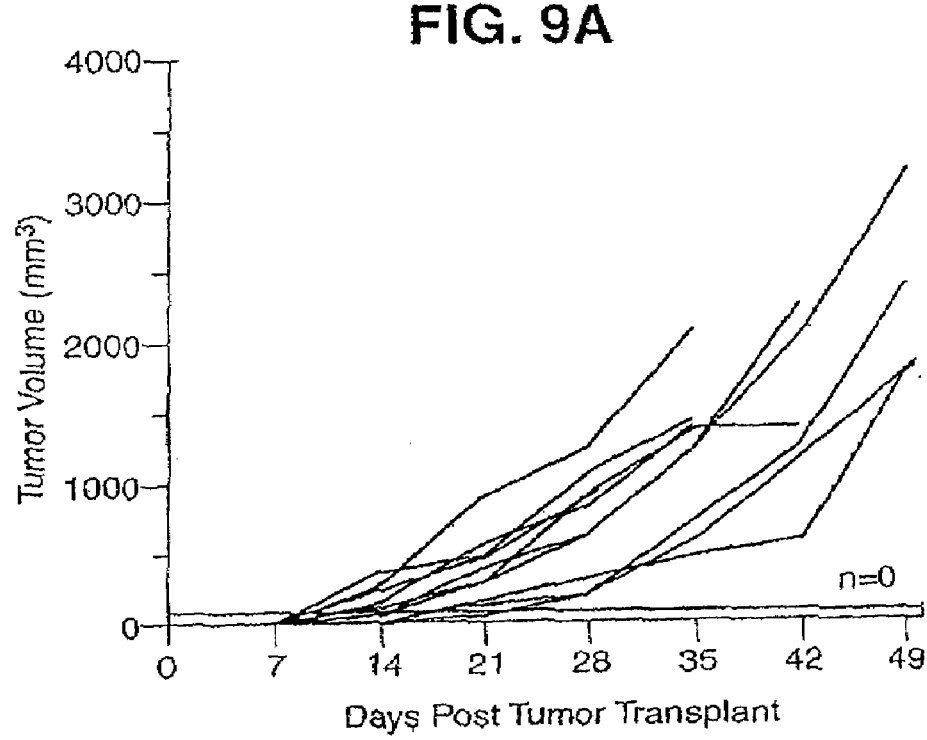
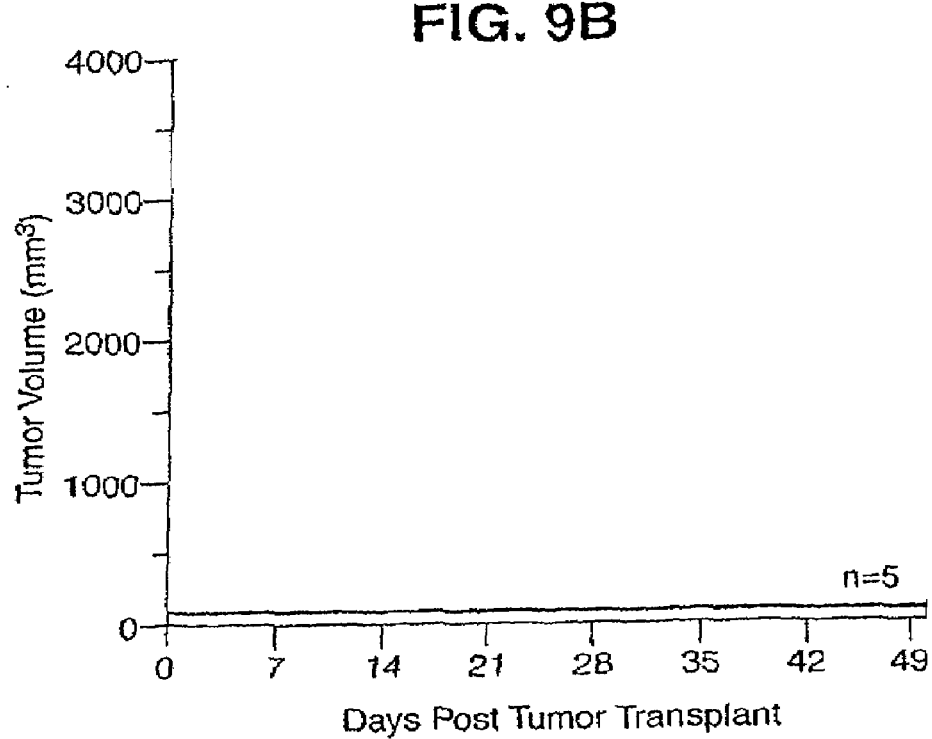

METHOD OF ENHANCING A TARGETED IMMUNE RESPONSE AGAINST TUMORS

CROSS-REFERENCE TO RELATED APPLICATIONS

This patent application is a divisional of U.S. patent application Ser. No. 11/090,686, filed on Mar. 28, 2005, now U.S. Pat. No. 7,368,116, which is a continuation of U.S. patent application Ser. No. 10/341,431, filed on Jan. 14, 2003, now U.S. Pat. No. 6, 893,869, which is a divisional of U.S. patent application Ser. No. 09/480,340, filed on Jan. 7, 2000, now U.S. Pat. No. 6,548,068, which is a continuation of U.S. patent application Ser. No. 08/483,316, filed Jun. 7, 1995, now U.S. Pat. No. 6,045,802, which is a continuation-in-part of U.S. patent application Ser. No. 08/317,268 filed Oct. 3, 1994, abandoned, all of which are hereby incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 3 kiloByte ASCII (text) file named "702853SequenceListing_ST25.TXT." created on Apr. 17, 2008.

FIELD OF THE INVENTION

The present invention relates to a composition of recombinant viral vector vaccines for the prevention or treatment of pathogenic diseases and cancer. More particularly, it relates to a composition of recombinant viral vectors comprising genes encoding an antigen(s) and recombinant viral vectors comprising a gene(s) encoding am immunostimulatory molecule(s). These genes can be inserted into one recombinant vector or separate viral vectors. Another aspect of the present invention is enhancing the immune response against disease cells (such as tumor cells) in a mammal by the infection of these cells with a recombinant vector containing an immunostimulatory gene(s) either in situ, or in vitro and the reintroduction of infected cells into the host.

BACKGROUND OF THE INVENTION

Attempts to elicit active immune responses in cancer patients to date can be classified as "non-specific" (i.e., the use of BCG) or "specific", i.e., the use of tumor cells, tumor cell extracts, mixtures of antigens from cell culture supernatant fluids or oncolysates of tumor cells. The vast majority of these efforts have been pursued in patients with metastatic melanoma. The development of a recombinant vaccine implies the use of specific and defined gene products or epitopes of an immunogen or an immunostimulatory molecule. Recombinant vaccines can also be used for "gene therapy" in that the latter approach requires using cells from a given patient and the insertion of a gene for an immunostimulatory molecule such as B7.1, B7.2, IL-2 or GM-CSF into those cells, either in situ or for administration of cultured cells back to the patient.

Recombinant vaccines can take many forms. Recombinant proteins can be synthesized by vectors such as baculovirus (an insect vector) or in eukaryotic cells. Synthetic peptides can also serve as immunogens. Peptide vaccines which consist of 9 to several dozen amino acids can take two forms. They can be mixed with adjuvant or they can be used to pulse peripheral, blood cells as antigen presenting cells (APCs) for reinfusion into the patient. Recombinant vaccines can also be constructed by inserting the gene which codes for a given tumor associated antigen into a vector. Some of the common vectors used are vaccinia virus, avian pox viruses such as fowlpox or canary pox, BCG, adenovirus and *Salmonella*. These vectors, each with their advantages and disadvantages are usually employed because of the immunogenicity of their constitutive proteins, thus rendering the protein or epitope of the inserted gene more immunogenic. Recombinant vaccines can also take the form of an anti-idiotype antibody which is directed against a monoclonal antibody prepared against a given tumor associated antigen. Most recently, polynucleotide vaccines have been prepared which consist of naked DNA of a tumor associated gene in a plasmid containing a promoter gene. Whereas all of the above have been analyzed in animal models, very few studies have compared relative efficiencies of one approach versus the other. Clinical trials have now begun using some of these approaches in breast cancer and other carcinoma patients and others will most likely begin in the near future.

There are several antigens that have now been identified for potential use in recombinant vaccines for cancer therapies. The first of these is the c-erbB/2 oncogene which is found to be over expressed in approximately 20-30% of breast tumors (Pietras R J et al. Oncogene (9:1829-1838, 1994). It has been shown (Bernards R et al. Proc. Natl. Acad. Sci. USA 84:6854-6858, 1987) that the point mutated c-erbB/2 oncogene in rats, when inserted into vaccinia virus, is immunogenic and can lead to anti-tumor effects. The human c-erbB/2, however, is not mutated. It has recently been shown (Disis M L et al., Cancer Res. 54:1071-1076, 1994)), that this gene contains several epitopes which appear to generate human T cell responses in vitro. The point mutated p53 oncogene, also found in many human breast tumors has been shown to be a potential target for cytotoxic T-cells (Yanuck M et al. Cancer Res. 53:3257-3261, 1993). Clinical studies are now beginning in which peptides reflecting specific point mutations are being pulsed with human peripheral blood lymphocytes (PBLs) and readministered to patients. The breast cancer mucin, MUC-1 or DF3, represents a differentiation antigen of the breast (Abe M and Kufe D, Proc. Natl. Acad. Sci. USA 90:282-286, 1993). While MUC-1 is expressed in a range of normal epithelial tissues, it appears to be uniquely glycosylated in breast cancer tissue. The tandem repeat of the core protein of the MUC-1 mucin has been reported to be immunogenic in humans (Barnd D L et al., Proc. Natl. Acad. Sci. USA 86:7159-7163, 1989) in that lymph nodes of breast cancer patients contain T-cells which can be activated by MUC-1 peptides in an non-MHC restricted manner. It has also been shown (Rughetti A et al., Cancer Res. 53:2457-2459, 1993) that ovarian cancer patients can make antibody responses to this region. Animal models in which the MUC-1 gene has been inserted into vaccinia virus have been reported (Hareuveni M et al., Proc. Natl. Acad. Sci. USA 87:9498-9502, 1990; Hareuveni et al., Vaccine 9:618-626, 1991). A clinical trial in which MUC-1 peptide is being pulsed with human PBLs is currently underway in breast cancer patients. Another mucin that represents a potential target for cancer therapy is TAG-72 which is found on approximately 70-80% of human breast cancers (Thor A et al., Cancer Res. 46:3118-3124, 1986).

Most attempts at active immunization against cancer antigens have involved whole tumor cells or tumor cell fragments, though it would be most desirable to immunize specifically against unique tumor antigens that distinguish malignant from normal cells. The molecular nature of the tumor associated antigens recognized by T lymphocytes is poorly understood. In contrast to antibodies that recognize epitopes or intact proteins, T cells recognize short peptide fragments (8-18 amino acids) that are present on cell surface class I or II major histocompatibility (MHC) molecules and it is likely that tumor associated antigens are presented and recognized by T cells in this fashion.

A number of genes have been identified that encode melanoma tumor antigens recognized by TIL in the context of the HLA-A2 class I molecule (Kawakami Y. et al. Proc. Natl. Acad. Sci. USA 91:3515-3519, 1994; Kawakami Y. et al. J. Exp. Med 180:347-352, 1994; Kawakami Y. et al. Cancer Res. 54:3124-3126, 1994).

The human carcinoembryonic antigen (CEA) also represents a potential target molecule for the immunotherapy of a range of human carcinomas including colorectal, gastric, pancreatic, breast, and non-small cell carcinomas (Robbins P F et al., Int. J. Cancer 53:892-897, 1993; Esteban J M et al., Cancer 74:1575-1583, 1994). Experimental studies have shown that anti-idiotype antibodies directed against anti-CEA monoclonal antibodies can elicit immune responses in mice (Bhattacharya-Chatterjee M et al., Int. Rev. Immuno. 7:289-302, 1991). Clinical studies using this anti-idiotype antibody are currently in progress. A recombinant vaccine has also been developed in which the CEA gene has been inserted into vaccinia virus (Kantor J. et al., J. Natl. cancer Inst. 84:1084-1091, 1992). A Phase I clinical trial involving this vaccine has just been completed.

The identification of an immunodominant peptide that represents a unique tumor antigen has opened new possibilities for immunization against cancer. Substantial evidence exists in animal models that immunization with immunodominant viral peptides can induce viral specific CTL that can confer protection against viral infection. Although pure peptide alone is ineffective in stimulating T cell responses, peptides emulsified in adjuvants or complexed with lipids have been shown to prime mice against challenge with fresh virus and can induce virus specific CTL that protect mice against lethal viral inocula (Kast, W. M. et al Proc. Nat'l Acad. Sci. U.S.A. 88:2283-2287, 1991; Deres, K. et al Nature 342:561-564, 1989; Gao, X. M. et al J. Immunol. 147:3268-3273, 1991; Aichele, P. J. J. Exp. Med. 171:1815-1820, 1990; Collins, D. S. et al J. Immunol. 148:3336-3341, 1992). Immunization of mice against splenocytes coated with *Listeria monocytogenes* peptide epitopes also results in the generation of *Listeria* specific CTL which can be expanded in culture. Adoptive transfer of these CTL can protect mice against lethal bacterial challenge (Harty, J. T. et al J. Exp. Med. 175:1531-1538, 1992). Peptides representing antigenic epitopes of HIV gp120 and gp160 emulsified in complete Freund's adjuvant can also prime specific CTL responses (Takahashi, H. et al Proc. Nat'l Acad. Sci. U.S.A. 85:3105-3109, 1988; Hart, M. K. et al Proc. Nat'l Acad. Sci. U.S.A. 88:9448-9452, 1991).

While immunization with peptides in adjuvants or complexed with lipids gives rise to T cell responses in mice, the reactions are rarely strong enough to induce T reactive cells in primary splenocytes. The detection of sensitized lymphocytes almost invariably requires secondary in vitro stimulation.

The expression of the B7 gene family has been shown to be an important mechanism of antitumor responses in both mice and humans. It is now becoming apparent that at least two signals are required for activation of naive T-cells by antigen bearing target cells: an antigen specific signal, delivered through the T-cell receptor, and an antigen independent or costimulatory signal leading to lymphokine products (Hellstrom, K. E. et al., Annals NY Acad. Sci. 690:225-230, 1993). Two important costimulatory molecules are B7-1, which is the ligand for T-cell surface antigens CD28 and CTLA4 (Schwartz, R. H. Cell 71:1065-1068, 1992; Chen, L. et al. Cell 71:1093-1102, 1992; Freeman, G. J. et al. J. Immunol 143:2714-2722, 1989; Freeman, G. J. et al. J. Exp. Med. 174:625-631, 1991), and B7-2, an alternative ligand for CTLA4 (Freeman, G. J. et al. Science 262:813-960, 1993). To date, both murine B7-1 and B7-2 (Freeman, G. J. et al. J. Exp. Med. 174:625-631, 1991; Freeman, G. J. et al. Science 262: 813-960, 1995) and human B7-1 and B7-2 have been described (Freeman, G. J. et al. J. Immunol. 143:2714-2722, 1989; Freeman, G. J. et al Science 262:909-911, 1993). It is unclear at this time whether the costimulatory signals provided by B7-1 and B7-2 are functionally distinct or redundant mechanisms for T-cell activation (Hathcock, K. S. et al. J. Exp. Med. 180:631-640, 1994). Most murine and human tumors do not express B7-1 or B7-2, implying that even when a tumor expresses a potential rejection antigen, it is unlikely to activate antitumor T-cell responses (Hellstrom, K. E. et al Annals. N.Y. Acad. Sci. 690:225-230, 1993); Hellstrom, I. Annals. N.Y. Acad. Sci. 690:24-31, 1993). In essence, anergy may result from only one signal being received by the T-cell (Hellstrom, K. e. et al. Annals. N.Y. Acad. Sci. 690:225-230, 1993. Transfection of B7 into melanoma cells was found to induce the rejection of a murine melanoma in vivo (Townsend, S. E. et al Science 259:368-370, 1993).

Vaccinia viruses have been extensively used in humans and the use of a vaccinia based vaccine against smallpox has led to the worldwide eradication of this disease (reviewed in reference Moss, B. Science 252:1662-1667, 1991). Vaccinia viruses have the advantages of low cost, heat stability and a simple method of administration. Attempts have been made to develop vaccinia virus vectors for the prevention of other diseases.

Vaccinia virus is a member of the pox virus family of cytoplasmic DNA viruses. DNA recombination occurs during replication of pox viruses and this has been used to insert DNA into the viral genome. Recombinant vaccinia virus expression vectors have been extensively described. These vectors can confer cellular immunity against a variety of foreign gene products and can protect against infectious diseases in several animal models. Recombinant vaccinia viruses have been used in human clinical trials as well. Cooney et al immunized 35 healthy HIV seronegative males with a recombinant vaccinia virus expressing the gp160 envelope gene of HIV (Cooney, E. The Lancet 337:567-572, 1991). Graham et al randomized 36 volunteers to receive either recombinant vaccinia virus containing the gp160 HIV envelope protein or control vaccinia virus (Graham, B. S. et al J. Infect. Dis. 166:244-252, 1992). Phase I studies using recombinant vaccinia virus have begun in patients with metastatic melanoma using a recombinant virus expressing the p97 melanoma antigen (Estin, C. D. et al Proc. Nat'l Acad. Sci. 85:1052-1056, 1988) and a Phase I trial to use recombinant vaccinia virus expressing the human carcinoembryonic antigen in patients with advanced breast, lung or colorectal carcinoma has just been completed. In these trials, vaccinia virus is administered by intradermal scarification and side effects have been minimal including local skin irritation, lymphadenopathy and transient flu-like symptoms.

Fowlpox and canarypox viruses are members of the pox virus family (avipox virus genes). These viruses will only replicate in avian cells and cannot replicate in human cells. They are cytoplasmic viruses that do not integrate into the host genome but are capable of expression of a large number of recombinant genes in eukaryotic cells.

Recombinant avian pox virus expressing rabies glycoprotein has been used to protect mice, cats and dogs against live rabies virus challenge. Immunization of chickens and turkeys with a recombinant avian pox expressing the influenza HA antigen protected against a lethal challenge with influenza virus (Taylor et al., Vaccine 6:504-508, 1988). Canarypox volunteers received doses up to $10^{5.5}$ infectious units (Cadoz M., et al., The Lancet 339:1429-1432, 1992). In a recent trial sponsored by NIAID (Protocol 012A: A Phase I safety and immunogenicity trial of live recombinant canarypox-gp 160 MN (ALVAC VCP125 HIV-1gp160MNO in HIV-1 uninfected adults) patients received recombinant canarypox virus containing the HIV gp160 gene by intramuscular injection at doses up to $10^{5.5}$ pfu with little or no toxicity (personal communication, P. Fast, NIAID).

Avian pox viruses thus represent attractive vehicles for immunization since they can stimulate both humoral and cellular immunity, can be economically produced in high titer ($10^9$ pfu/ml) and yet their inability to productively infect human cells substantially increases the safety of their use.

Another considerable advantage of avian pox virus is that there may be little or no cross-reactivity with vaccinia virus and thus previously vaccinated humans may not have preexisting immune reactivity to fowlpox virus proteins.

SUMMARY OF THE INVENTION

The present invention relates to a composition of recombinant viral vector vaccines for the prevention or treatment of pathogenic diseases and cancer. More particularly, it relates to a composition of recombinant viral vectors comprising genes encoding an antigen(s) and recombinant viral vectors comprising a gene(s) encoding an immunostimulatory molecule(s). These genes can be inserted into one recombinant vector or separate viral vectors. Another aspect of the present invention is enhancing the immune response against disease cells (such as tumor cells) in a mammal by the infection of these cells with a recombinant vector containing an immunostimulatory gene(s) either in situ, or in vitro and the reintroduction of infected cells into the host.

BRIEF DESCRIPTION OF THE DRAWINGS

These and other objects, feature and many of the attendant advantages of the invention will be better understood upon a reading of the detailed description of the invention when considered.

FIGS. 1A and 1B are representative of B7 staining on normal BSC-1 cells or cells infected with the parent vaccinia strain used to construct rV-B7-1 and rV-B7-2, while FIGS. 1C and 1D illustrate strong expression of recombinant B7 proteins after infection with rV-B7-1 or rV-B7-2, using monoclonal antibodies specific for these molecules, respectively.

FIGS. 2A and 2B illustrate normal growth rates of MC38 cells. FIGS. 2C and 2D illustrate growth rates of MC38 cells expressing recombinant B7 proteins. Tumors were measured in two dimensions. These experiments were repeated 3 additional times with similar results. *Animal grew an intraperitoneal tumor which could not be measured.

FIG. 3A shows growth of uninfected MC38 tumors in naive C57BL/6 mice. FIG. 3B shows growth of MC38 tumors in mice previously administered (day 40) with MC38 cells infected with rV-B7-1 and challenged with $3 \times 10^5$ MC38 cells. FIG. 3C shows growth of MC38 tumors in mice previously administered (day 40) with MC38 cells infected with rV-B7-2 and challenged with $3 \times 10^5$ MC38 cells.

FIGS. 6A-6D show the fluorescent analysis of BSC-1 cells co-infected with rV-CEA and rV-B7. BSC-1 cells were co-infected with virus at an MOI of 5 in ratios of either: 6A) V-Wyeth; 6B) rV-CEA:V-Wyeth (3:1); 6C) Wyeth:rV-B7 (3:1); or 6D) rV-CEA:rV-B7 (3:1) and stained with MAbs PE-B7-1 and FITC-COL-1. X and Y axes represent CEA and B7-1 fluorescence respectively, while the Z axis represents cell number. Percentages of positive cells in each quadrant are depicted in inset panels. FIG. 6A depicts staining on normal BSC-1 cells infected with the parent vaccinia stain. FIGS. 6B and 6C depict expression of CEA or B7-1 during single infections, while FIG. 6D illustrates co-expression of both recombinant molecules following infection with both rV-CEA and rV-B7.

FIGS. 8A-8D show growth of transplanted mouse adenocarcinoma cells expressing CEA in mice immunized with rV-CEA and rV-B7. 10C57BL/6 mice per group were immunized one time with a total of $10^7$ PFU of either 8A) V-Wyeth; 8B) rV-CEA:V-Wyeth (3:1); 8C) Wyeth:rV-B7 (3:1); or 8D rV-CEA:rV-B7 (3:1), and injected 14 days later with $3\times10^5$ MC-38-CEA-2 cells subcutaneously.

FIGS. 9A-9B show antitumor immunity in mice previously receiving a mixture of rV-B7 and rV-CEA. FIG. 9A shows growth of MC-38-CEA-2 tumors in naive C57BL/6 mice, and tumor growth in mice surviving previous tumor challenge (FIG. 9B). Mice were immunized with rV-CEA:rV-B7 (3:1), and challenged with tumor 14 days later. Mice remaining tumor free after 60 days (FIG. 8D), were rechallenged on the opposite flank (FIG. 9B).

DETAILED DESCRIPTION OF THE INVENTION

Figure 1A:
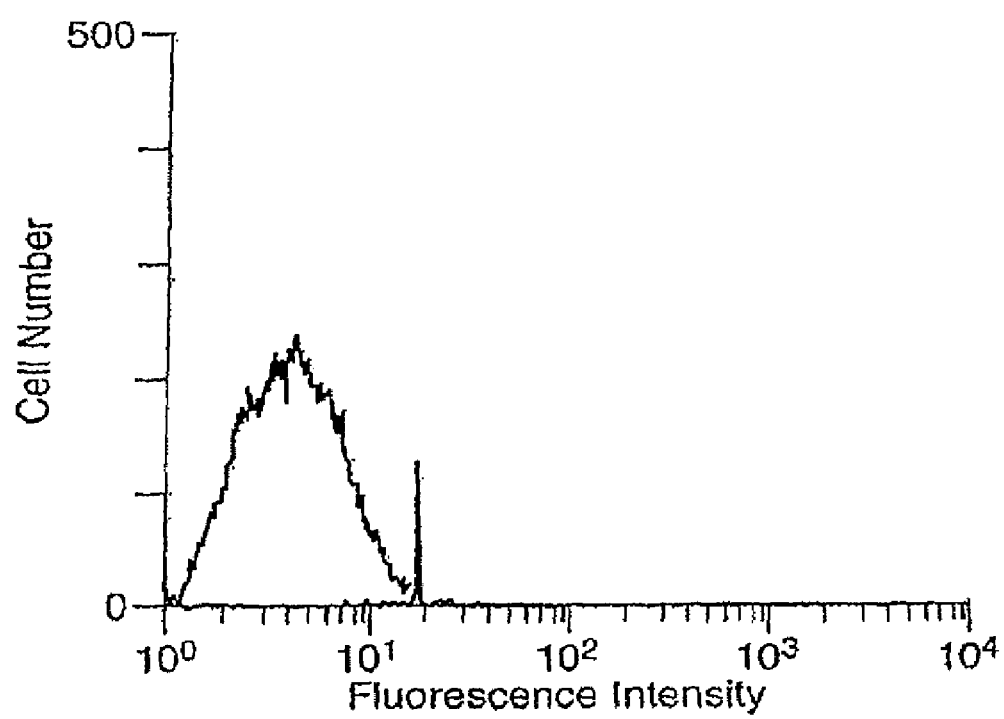
FIGS. 1A-1D shows Fluorescent Analysis of BSC-1 cells expressing rV-B7 proteins. BSC-1 cells were stained for either B7-1 or B7-2 surface proteins before infection (FIG. 1A), after infection with either 10 MOI V-Wyeth (FIG. 1B), rV-B7-1 (FIG. 1C), or rV-B7-2 (FIG. 1D).

The present invention is a composition comprising a novel recombinant virus expressing an antigen(s) from a disease causing agent or disease state and a recombinant virus expressing an immunostimulatory molecule(s) or genes coding for both molecules inserted in the same vector composition is capable of eliciting and/or upregulating an immune response in a mammal to T-dependent antigens or antibodies for the purpose of preventing or treating a disease. The composition of the present invention is particularly important in upregulating cell-mediated immunity as well as antibodies.

Cell-mediated immunity is crucial to resistant diseases caused by cancer and pathogenic microorganisms, particularly viruses and other intracellular microorganisms. The composition of the present invention has a first recombinant virus which has incorporated into its genome or portion thereof a gene encoding an antigen from cells of a disease state and a second recombinant virus which has one or more genes encoding one or more immunostimulatory molecules or genes coding for both molecules inserted into the same vector. A host cell infected with both recombinant viruses expresses both the antigen(s) from a disease causing agent and expresses the immunostimulatory molecule(s). The antigen may be expressed at the cell surface of the infected host cell. The immunostimulatory molecule may be expressed at the cell surface or may be actively secreted by the host cell.

The expression of both the antigen and the immunostimulatory molecule provides the necessary MHC restricted peptide to specific T cells and the appropriate signal to the T cell to aid in antigen recognition and proliferation or clonal expansion of antigen specific T cells. The overall result is an upregulation of the immune system. In a preferred embodiment the upregulation of the immune response is an increase in antigen specific T-helper lymphocytes and/or cytotoxic lymphocytes, which are able to kill or inhibit the growth of a disease causing agent or a cell infected with a disease causing agent.

In one embodiment, the composition comprises a recombinant virus comprising the virus genome or portions thereof and a nucleic acid sequence encoding an antigen from a pathogenic microorganism and a recombinant virus comprising one or more nucleic acid sequences encoding one or more immunostimulatory molecules.

In another embodiment, the composition comprises a recombinant virus comprising the virus genome or portions thereof and the nucleic acid sequence encoding a tumor associated antigen, and a recombinant virus encoding one or more nucleic acid sequences encoding one or more immunostimulatory molecules.

In one embodiment the recombinant viruses have been constructed to express cytokines (TNF-α, IL-6, GM-CSF, and IL-2), and co-stimulatory and accessory molecules (B7-1, B7-2) alone and in a variety of combinations. Simultaneous production of an immunostimulatory molecule and the model TAA at the site of virus replication/infection (in any case, the site of TAA production) enhances the generation of specific effectors. Dependent upon the specific immunostimulatory molecules, different mechanisms might be responsible for the enhanced immunogenicity: augmentation of help signal (IL-2), recruitment of professional APC (GM-CSF), increase in CTL frequency (IL-2), effect on antigen processing pathway and MHC expression (IFNγ and TNFα) and the like. The co-expression of a model antigen together with at least one immunostimulatory molecule is effective in an animal model to show anti-tumor effects.

In some cases it may be beneficial to make a recombinant virus comprising more than one antigen of interest for the purpose of having a multivalent vaccine. For example, the recombinant virus may comprise the virus genome or portions thereof, the nucleic acid sequence encoding GP120 (from HIV) and the nucleic acid sequence encoding Hep B surface antigen.

In one embodiment, the composition comprises a recombinant virus comprising a vaccinia virus genome or portions thereof, the nucleic acid sequence encoding CEA and a recombinant virus comprising the nucleic acid sequence encoding the immunostimulatory molecule, B 7.1 alone or in combination with the nucleic acid sequence encoding the immunostimulatory molecule, B7.2, or a recombinant virus containing both the genes for a tumor antigen and a immunostimulatory molecule.

The present invention also encompasses a recombinant virus comprising the virus genome or portion thereof, and one or more nucleic acid sequences encoding one or more B7 molecules, preferably a recombinant vaccinia virus expressing B7-1 and/or B7-2. The rapid infection of tumor cells with these recombinant viruses demonstrates that vaccinia can authentically express these proteins and that they are functional molecules. Weakly immunogenic syngeneic tumors expressing these recombinant molecules are rejected by immunocompetent hosts.

In a specific embodiment recombinant virus is a recombinant vaccinia virus containing B7.1 and a recombinant vaccinia virus containing B7.2 (designated rV-B7-1 and rV-B7-2, respectively).

In one embodiment the composition comprises rV-B7-1 and/or rV-B7.2 in combination with rV-CEA. The B7 molecule includes but is not limited to B7-1, B7-2 and the like and analogs thereof. The B7 gene may be cloned from mammalian sources, including but not limited to mammalian tissues, genomic libraries or cDNA libraries, preferably from murine or human sources.

Virus Vectors

Virus that may be used in the present invention are those in which a portion of the genome can be deleted to introduce new genes without destroying infectivity of the virus. The virus vector of the present invention is a nonpathogenic virus. In one embodiment the virus vector has a tropism for a specific cell type in the mammal. In another embodiment, the virus vector of the present invention is able to infect professional antigen presenting cells such as dendritic cells and macrophages. In yet another embodiment of the present invention, the virus vector is able to infect any cell in the mammal. The virus vector may also infect tumor cells.

The virus of the present invention include but is not limited to Poxvirus such as vaccinia virus, fowlpox virus and a highly attenuated vaccinia virus (MVA), adenovirus, baculovirus and the like.

The vaccinia virus genome is known in the art. It is composed of a HIND F13L region, TK region, and an HA region. The recombinant vaccinia virus has been used in the art to incorporate an exogenous gene for expression of the exogenous gene product (Perkus et al. *Science* 229:981-984, 1985; Kaufman et al. *Int. J. Cancer* 48:900-907, 1991; Moss *Science* 252:1662, 1991)

A gene encoding an antigen of a disease state or disease causing agent may be incorporated into the HIND F13L region or alternatively incorporated into the TK region of recombinant vaccinia virus vector or other nonessential regions of the vaccinia virus genome. Likewise, a gene encoding an immunostimulatory molecule may be incorporated into the HIND F13L region or the TK region of recombinant vaccinia virus vector.

Sutter and Moss (*Proc. Nat'l. Acad. Sci. U.S.A.* 89:10847-10851, 1992) and Sutter et al. (*Virology* 1994) disclose the construction and use as a vector, the non-replicating recombinant Ankara virus (MVA, modified vaccinia Ankara) which may be used as a viral vector in the present invention.

Baxby and Paoletti (*Vaccine* 10:8-9, 1992) disclose the construction and use as a vector, of the non-replicating poxvirus, including canarypox virus, fowlpox virus and other avian species which may be used as a viral vector in the present invention.

Expression vectors suitable for use in the present invention comprise at least one expression control element operationally linked to the nucleic acid sequence. The expression control elements are inserted in the vector to control and regulate the expression of the nucleic acid sequence. Examples of expression control elements includes, but is not limited to, lac system, operator and promoter regions of phage lambda, yeast promoters and promoters derived from polyoma, adenovirus, retrovirus or SV40. Additional preferred or required operational elements include, but are not limited to, leader sequence, termination codons, polyadenylation signals and any other sequences necessary or preferred for the appropriate transcription and subsequent translation of the nucleic acid sequence in the host system. It will be understood by one skilled in the art the correct combination of required or preferred expression control elements will depend on the host system chosen. It will further be understood that the expression vector should contain additional elements necessary for the transfer and subsequent replication of the expression vector containing the nucleic acid sequence in the host system. Examples of such elements include, but are not limited to, origins of replication and selectable markers. It will further be understood by one skilled in the art that such vectors are easily constructed using conventional methods (Ausubel et al., (1987) in "Current Protocols in Molecular Biology", John Wiley and Sons, New York, N.Y.) or commercially available.

Disease Causing Agents

The recombinant virus of the present invention is effective in treating or preventing disease caused by disease causing agents. Each disease causing agent or disease state has associated with it an antigen or immunodominant epitope on the antigen which is crucial in immune recognition and ultimate elimination or control of the disease causing agent or disease state in a host, sometimes referred to in the art as a protective antigen. The host immune system must come in contact with the antigen or immunodominant epitope on the antigen in order to mount a humoral and/or cellular immune response against the associated disease causing agent.

The composition of the present invention comprises a recombinant virus of the present invention comprises one or more nucleic acid sequences encoding one or more isolated antigens or immunodominant epitopes and a second recombinant virus comprises one or more immunostimulatory molecules.

Such disease causing agents include but are not limited to cancer and pathogenic microorganisms. Cancers which may be treated using the recombinant virus of the present invention include but are not limited to primary or metastatic melanoma, thymoma, lymphoma, sarcoma, lung cancer, liver cancer, non-Hodgkins lymphoma, Hodgkins lymphoma, leukemias, uterine cancer, and adenocarcinomas such as breast cancer, prostate cancer, ovarian cancer, pancreatic cancer and the like.

The aforementioned cancers can be assessed or treated by methods described in the present application. In the case of cancer, a gene encoding an antigen associated with the cancer is incorporated into the recombinant virus genome or portion thereof along with a gene encoding one or more immunostimulatory molecules. Alternatively, the gene encoding an antigen associated with the cancer and the gene encoding one or more immunostimulatory molecules are incorporated into separate recombinant viruses. The antigen associated with the cancer may be expressed on the surface of a cancer cell or may be an internal antigen. In one embodiment the antigen associated with the cancer is a tumor associated antigen (TAA) or portion thereof. Examples of TAA that may be used in the present invention include but are not limited to melanoma TAAs which include but are not limited to MART-1 (Kawakami et al. *J. Exp. Med.* 180:347-352, 1994), MAGE-1, MAGE-3, GP-100, (Kawakami et al. *Proc. Nat'l. Acad. Sci. U.S.A.* 91:6458-6462, 1994), CEA and tyrosinase (Brichard et al. *J. Exp. Med.* 178:489, 1993).

In another embodiment the TAAs are MUC-1, MUC-2, the point mutated ras oncogene and the point mutated p53 oncogenes (pancreatic cancer), CA-125 (ovarian cancer), PSA (prostate cancer), c-erb/B2 (breast cancer) and the like (Boon et al., Ann. Rev. Immunol. 12:337, 1994).

The present invention is in no way limited to the genes encoding the above listed TAAs. Other TAAs may be identified, isolated and cloned by methods known in the art such as those disclosed in U.S. Pat. No. 4,514,506.

Genes encoding an antigen of a disease causing agent in which the agent is a pathogenic microorganism include viruses such as HIV (GP-120, p17, GP-160 antigens), influenza (NP, HA antigen), herpes simplex (HSVdD antigen), human papilloma virus, equine encephalitis virus, hepatitis (Hep B Surface Antigen) and the like. Pathogenic bacteria include but are not limited to *Chlamydia, Mycobacteria, Legioniella* and the like. Pathogenic protozoans include but are not limited to malaria, *Babesia, Schistosomiasis* and the like. Pathogenic yeast include *Aspergillus*, invasive *Candida*, and the like. In a preferred embodiment the pathogenic microorganism is an intracellular organism.

Immunostimulatory Molecules: Costimulation/Accessory Molecules and Cytokines

The gene from costimulation/accessory molecule and/or gene encoding an a cytokine is incorporated into the genome of a recombinant virus. Examples of costimulation molecules include but are not limited to B7-1, B7-2, ICAM-1, LFA-3, CD72 and the like. Examples of cytokines encompassed by the present invention include but are not limited to IL-2, GM-CSF, TNFα, IFNγ, IL-12, RANTES, and the like.

IL-2 Construct

The IL-2 gene of the present invention is made as disclosed by Taniguchi et al (*Nature* 302:305, 1983).

B7 Construct

Co-stimulatory molecules of the B7 family (namely B7.1, B7.2, and possibly B7.3) represent a more recently discovered, but important group of molecules. B7.1 and B7.2 are both member of the Ig gene superfamily. These molecules are present on macrophages, dendritic cells, monocytes, i.e., antigen presenting cells (APCs). If a lymphocyte encounters an antigen alone, with co-stimulation by B7.1, it will respond with either anergy, or apoptosis (programmed cell death); if the co-stimulatory signal is provided it will respond with clonal expansion against the target antigen. No significant amplification of the immune response against a given antigen occurs without co-stimulation (June et al. (*Immunology Today* 15:321-331, 1994); Chen et al. (*Immunology Today* 14:483-486); Townsend et al. (*Science* 259:368-370)). Freeman et al. (*J. Immunol.* 143:2714-2722, 1989) report cloning and sequencing of B7.1 gene. Azuma et al. (*Nature* 366:76-79, 1993) report cloning and sequencing B7.2 gene.

In one embodiment the B7.1 gene or the B7.2 gene was inserted into vaccinia virus. In another embodiment, the CEA gene and the IL-2 gene were both inserted into a single vaccinia virus. The rV-CEA/$_n$IL-2 (ATCC Designation VR 2480), rV-CEA-T108 (ATCC Designation No. VR 2481), rV-$_m$B7-2 (ATCC Designation VR 2482); and rV-$_m$B7-1 (ATCC Designation VR 2483) were deposited with the American Type Culture Collection (ATCC), 12301 Parklawn Drive, Rockville, Md. on Oct. 3, 1994 under the terms of the Budapest Treaty.

The present invention also encompasses methods of treatment or prevention of a disease caused by the disease causing agents or disease states disclosed here.

In the method of treatment, the administration of the recombinant virus of the invention or composition of recombinant viruses may be for either "prophylactic" or "therapeutic" purpose. When provided prophylactically, the recombinant virus or composition of recombinant viruses of the present invention is provided in advance of any symptom. The prophylactic administration of the recombinant virus or composition of recombinant viruses serves to prevent or ameliorate any subsequent infection or disease. When provided therapeutically, the recombinant virus or composition of more than one recombinant virus is provided at (or shortly after) the onset of a symptom of infection or disease. Thus the present invention may be provided either prior to the anticipated exposure to a disease causing agent or disease state or after the initiation of the infection or disease.

The genetic definition of tumor-specific antigens allows for the development of targeted antigen-specific vaccines for cancer therapy. Insertion of a tumor antigen gene in the genome of viruses in combination with a recombinant virus comprising an immunostimulatory molecule is a powerful system to elicit a specific immune response in terms of prevention in patient with an increased risk of cancer development (preventive immunization), prevention of disease recurrence after primary surgery (anti-metastatic vaccination), or as a tool to expand the number of CTL in vivo, thus improving their effectiveness in eradication of diffuse tumors (treatment of established disease). Finally, recombinant viruses or composition of the present invention can elicit an immune response in patient that is enhanced ex vivo prior to being transferred back to the tumor bearer (adoptive immunotherapy).

The term "unit dose" as it pertains to the inoculum refers to physically discrete units suitable as unitary dosages for mammals, each unit containing a predetermined a quantity of recombinant virus calculated to produce the desired immunogenic effect in association with the required diluent. The specifications for the novel unit dose of an inoculum of this invention are dictated by and are dependent upon the unique characteristics of the recombinant virus and the particular immunologic effect to be achieved.

The inoculum is typically prepared as a solution in tolerable (acceptable) diluent such as saline, phosphate-buffered saline or other physiologically tolerable diluent and the like to form an aqueous pharmaceutical composition.

The route of inoculation may be intravenous (I.V.), intramuscular (I.M.), subcutaneous (S.C.), intradermal (I.D.) and the like, which results in eliciting a protective response against the disease causing agent. The dose is administered at least once. Subsequent doses may be administered as indicated.

In providing a mammal with the recombinant virus of the present invention, preferably a human, the dosage of administered recombinant virus will vary depending upon such factors as the mammal's age, weight, height, sex, general medical condition, previous medical history, disease progression, tumor burden and the like.

In general, it is desirable to provide the recipient with a dosage of each recombinant virus in the composition in the range of from about $10^5$ to about $10^{10}$ plaque forming units/mg mammal, although a lower or higher dose may be administered.

The composition of recombinant viral vectors can be introduced into a mammal either prior to any evidence of cancers such as melanoma or to mediate regression of the disease in a mammal afflicted with a cancer such as melanoma. Examples of methods for administering the composition into mammals include, but are not limited to, exposure of cells to the recombinant virus ex vivo, or injection of the composition into the affected tissue or intravenous, S.C., I.D. or I.M. administration of the virus. Alternatively the recombinant viral vector or combination of recombinant viral vectors may be administered locally by direct injection into the cancerous lesion or topical application in a pharmaceutically acceptable carrier. The quantity of recombinant viral vector, carrying the nucleic acid sequence of one or more TAAs to be administered is based on the titer of virus particles. A preferred range of the immunogen to be administered is $10^5$ to $10^{10}$ virus particles per mammal, preferably a human.

In the case where a combination of a first recombinant viral vector carrying a nucleic acid sequence of one or more TAAs and a second recombinant viral vector carrying the nucleic acid sequence of one or more immunostimulatory molecules is used, the mammal may be immunized with different ratios of the first and second recombinant viral vector. In one embodiment the ratio of the first vector to the second vector is about 1:1, or about 1:3, or about 1:5. Optimal ratios of the first vector to the second vector may easily be titered using the methods described herein.

After immunization the efficacy of the vaccine can be assessed by production of antibodies or immune cells that recognize the antigen, as assessed by specific lytic activity or specific cytokine production or by tumor regression. One skilled in the art would know the conventional methods to assess the aforementioned parameters. If the mammal to be immunized is already afflicted with cancer or metastatic cancer the vaccine can be administered in conjunction with other therapeutic treatments.

In one method of treatment, autologous cytotoxic lymphocytes or tumor infiltrating lymphocytes may be obtained from a patient with cancer. The lymphocytes are grown in culture and antigen specific lymphocytes expanded by culturing in the presence of specific antigen and cytokine. The antigen specific lymphocytes are then reinfused back into the patient.

The present invention encompasses methods of enhancing antigen-specific T-cell responses by administration of an effective amount of an antigen in a recombinant virus in combination with an immunostimulatory molecule such as B7 in a recombinant virus into a mammal. This immunization approach augments or enhances immune responses generated by the antigen with costimulation by the B7 costimulatory molecule. The method of administering an antigen containing recombinant virus and a B7 containing recombinant virus results in increased antigen specific lymphoproliferation, enhanced cytolytic activity and long lasting immunity to the antigen as compared to the use of either recombinant virus alone. In one embodiment of the method of enhancing antigen-specific T-cell responses, mammals, preferably humans, are immunized with rV-TAA and rV-B7. The ratio of rV-TAA to rV-B7 may be varied to maximize the antigen-specific T-cell response. Ratios of rV-TAA to rV-B7 include but are not limited to 1:1, 2:1, 3:1, 4:1, and the like. The efficacy of the treatment may be monitored in vitro and/or in vivo by determining antigen specific lymphoproliferation, antigen-specific cytolytic response, tumor regression and the like.

The addition of any amount of rV-B7 to an antigen regardless of ratio results in improved cellular immunity. However, an optimal ratio of antigen to rV-B7 may be determined for each antigen of interest. In one embodiment, using a rV-CEA to rV-B7 the ratio resulting in the strongest increase in antigen specific lymphoproliferative, cytotoxic and antitumor responses specific for CEA was 3:1.

The method of enhancing antigen-specific T-cell responses may be used for any antigen. Of particular interest are tumor associated antigens and antigens of infectious agents. In one method of enhancing antigen-specific T-cell responses, rV-CEA and rV-human B7-1 are administered to a patient bearing a CEA positive carcinoma in an optimal ratio to stimulate CEA-specific T-cell responses resulting in reduction or elimination of the CEA positive carcinoma. In another method of enhancing antigen-specific T-cell responses, rV-gp120 or portions thereof and rV-human B7-1 are administered to a patient bearing gp120 positive cells in a ratio to stimulate gp120 specific T-cell responses resulting in reduction or elimination of gp120 positive cells.

The present invention also encompasses combination therapy. By combination therapy is meant that the composition of a recombinant virus comprising one or more genes encoding one or more antigens associated with one or more disease agents and a recombinant virus comprising one or more genes encoding one or more immunostimulatory molecules or both types of genes incorporated into the same vector are administered to the patient in combination with other exogenous immunomodulators or immunostimulatory molecules, chemotherapeutic drugs, antibiotics, antifungal drugs, antiviral drugs and the like alone or in combination thereof. Examples of other exogenously added agents include exogenous IL-2, IL-6, interferon, tumor necrosis factor, cyclophosphamide, and cisplatinum, gancyclovir, amphotericin B and the like.

Another aspect of the present invention is a method of treating cancer in which cancer cells are infected with the recombinant virus or combination of recombinant virus in situ or in vitro. Tumor cells expressing both the tumor associated antigen along with an immunostimulatory molecule are administered to a mammal in an effective amount to result in tumor reduction or elimination in the mammal afflicted with a cancer.

This invention further comprises an antibody or antibodies elicited by immunization with the recombinant virus of the present invention. The antibody has specificity for and reacts or binds with the antigen of interest. In this embodiment of the invention the antibodies are monoclonal or polyclonal in origin.

Exemplary antibody molecules are intact immunoglobulin molecules, substantially intact immunoglobulin molecules or those portions of an immunoglobulin molecule that contain the antigen binding site, including those portions of immunoglobulin molecules known in the art as F(ab), F(ab'); F(ab')$_2$ and F(v). Polyclonal or monoclonal antibodies may be produced by methods known in the art. (Kohler and Milstein (1975) *Nature* 256, 495-497; Campbell "Monoclonal Antibody Technology, the Production and Characterization of Rodent and Human Hybridomas" in Burdon et al. (eds.) (1985) "Laboratory Techniques in Biochemistry and Molecular Biology," Volume 13, Elsevier Science Publishers, Amsterdam). The antibodies or antigen binding fragments may also be produced by genetic engineering. The technology for expression of both heavy and light chain genes in *E. coli* is the subject of the PCT patent applications: publication number WO 901443, WO 901443 and WO 9014424 and in Huse et al. (1989) *Science* 246:1275-1281.

In one embodiment the antibodies of this invention are used in immunoassays to detect the novel antigen of interest in biological samples.

In one embodiment, the CEA antibodies of this invention generated by immunization with a composition comprising recombinant vaccinia virus expressing CEA and a recombinant vaccinia virus expressing B7.1 are used to assess the presence of the CEA antigen from a tissue biopsy of a mammal afflicted with a cancer expressing CEA using immunocytochemistry. Such assessment of the delineation of the CEA antigen in a diseased tissue can be used to prognose the progression of the disease in a mammal afflicted with the disease or the efficacy of immunotherapy. Conventional methods for immunohistochemistry are described in (Harlow and Lane (eds) (1988) In "Antibodies A Laboratory Manual", Cold Spinning Harbor Press, Cold Spring Harbor, N.Y.; Ausbel et al. (eds) (1987). In Current Protocols In Molecular Biology, John Wiley and Sons (New York, N.Y.).

In another embodiment the antibodies of the present invention are used for immunotherapy. The antibodies of the present invention may be used in passive immunotherapy.

In providing a patient with the antibodies or antigen binding fragments to a recipient mammal, preferably a human, the dosage of administered antibodies or antigen binding fragments will vary depending upon such factors as the mammal's age, weight, height, sex, general medical condition, previous medical condition and the like.

The antibodies or antigen-binding fragments of the present invention are intended to be provided to the recipient subject in an amount sufficient to prevent, lessen or attenuate the severity, extent or duration of the disease or infection.

Anti-idiotypic antibodies arise normally during the course of immune responses, and a portion of the anti-idiotype antibody resembles the epitope that induced the original immune response. In the present invention, the immunoglobulin gene or portion thereof of an antibody whose binding site reflects an antigen of a disease state, is incorporated into the genome or portion thereof of a virus genome, alone or in combination with a gene or portion thereof of an immunostimulatory molecule, the resulting recombinant virus is able to elicit cellular and humoral immune response to the antigen.

EXAMPLE 1

Construction and Characterization of Construction of rV-B7-1 and rV-B7-2

Materials and Methods

Recombinant Vaccinia Virus

A 1,125 bp DNA fragment encoding the entire open reading frame of murine B7-1 and a 942 bp DNA fragment encoding the entire open reading frame of murine B7-2 was amplified by reverse transcriptase PCR (Geneamp RNA PCR Kit, Perkin Elmer, Norwalk, Conn.) from total RNA extracted from the murine B-cell line, A20 (TIB 208, ATCC, Rockville, Md.). The sequences of the B7 inserts were shown to be identical to the published sequences (Freeman, G. J. et al. *J. Exp. Med.* 174:625-631, 1991; Freeman, G. J. et al. *Science* 262:813-960, 1993). The DNA fragments were ligated separately into the Kpn-1/Xho-1 restriction enzymes sites of the vaccinia virus transfer vector PT116, provided by Therion Biologics (Cambridge, Mass.) which contains the *Escherichia Coli* Lac Z gene for the selection of the recombinant viruses. Recombinant viruses were derived as previously described (Kaufman, H. et al. *Int. J. of Cancer* 48:900-907, 1991). Recombinant clones were selected by growth on BSC-1 cells (CC126, ATCC) in the presence of 5-bromo-4-chloro-3-indolyl-beta D galactosidase (X-Gal). Appropriate blue recombinant clones were purified by 5 rounds of plaque purification and grown into a higher titer lysate. Virus for inoculation was grown in spinner cultures of HeLa cells, directly pelleted by centrifugation, and purified over 20%-40% sucrose gradients (Moss, B. Current Protocols in Molecular Biology 2.16.15.1-16.18.9, 1993).

Characterization of Recombinant Virus

Southern Analysis of DNA Recombination

The recombinant vaccinia genomes were analyzed by viral DNA extraction, restriction endonuclease digestion with Hind III, and Southern blotting as previously described (Kaufman, H. et al. *Int. J. Cancer* 48:900-907, 1991).

Western Analysis of Protein Expression

Confluent BSC-1 cells were infected with either wild-type vaccinia virus or recombinant vaccinia viruses containing the murine B7-1 or B7-2 genes (designated V-Wyeth, rV-B7-1 or rV-B7-2) at an MOI of 10 for 4 hours. Protein was extracted and analyzed as described previously (Kantor, J. et al. *J. Nat'l Cancer Inst.* 84:1084-1091, 1992). Recombinant B7-1 or B7-2 protein was detected by incubating western blots with anti-B7-1 (purified Rat-Anti mouse B7/BB1) or anti-B7-2 (Rat-anti-mouse B7-2 (GL-1) monoclonal antibodies (Pharmingen, San Diego, Calif.), followed by incubation with Goat-anti-rat conjugated to horseradish peroxidase (HRP, Kirkegaard & Perry Laboratories, Gaithersburg, Md.) and developed as per manufacturers instructions.

Fluorescent Analysis of Protein Expression

Confluent BSC-1 cells were infected with either V-Wyeth, rV-B7-1 or rV-B7-2 at 10 MOI for 2 hours. Cells were harvested 3-6 hours post infection and immunostained with purified Rat-Anti-mouse B7/BB1'-FITC or Rat-anti-mouse B7-2 (GL-1)-FITC monoclonal antibodies. Cells were analyzed by flow cytometry (FACSCAN, Becton Dickinson, San Jose, Calif.).

In-Vivo Experiments

The MC38 murine clonic adenocarcinoma cell line (Fox, B. A. et al. *J. Biol. Response Modifiers* 9:499-511, 1990) was supplied by the laboratory of Dr. Steve Rosenberg (National Cancer Institute, Bethesda, Md.). MC38 cells were infected with either V-Wyeth, rV-B7-1 or rV-B7-2 at 0.25 MOI for 1 hour, washed, and suspended in HBSS at a concentration of $3 \times 10^6$ cells/ml. Female C57BL/6 mice were obtained from Taconic Farms (Germantown, N.Y.). Six to 8 weeks old animals were given a subcutaneous injection of 100 µl ($3 \times 10^5$ infected cells) in the right flank. Control mice were injected with uninfected MC38 cells. Mice remaining tumor free for at least 40 days were challenged on the opposite flank with $3 \times 10^5$ uninfected cells. In a parallel experiment, C57BL/6 mice were gamma irradiated (500 rad) and injected 24 hours later with either uninfected MC38 cells, or cells infected with 0.25 MOI V-Wyeth, rV-B7-1 or rV-B7-2. Tumors were measured by caliper in two dimensions, and the volumes calculated as previously described (Kantor, J. et al. *J. Nat'l Cancer Instit.* 84: 1984-1091, 1992).

EXAMPLE 2

Generation and Characterization of Recombinant Virus

The cDNA fragments encoding the open reading frames of murine B7-1 and B7-2 were obtained by reverse transcriptase PCR using B7-1 specific oligonucleotide primers 5' GGTAC-CATGGCTTGCAATTGTCAGTTG 3' (SEQ ID NO.:1), 5' CTCGAGCTAAAGGAAGACGGTCTG 3' (SEQ ID No.:2), and B7-2 specific primers 5' GGTACCGAAGCACCCAC-GATGGAC 3' (SEQ ID No.: 3), 5' CTCGAGTCACTCTG-CATTTGGTTTTGC 3' (SEQ ID No.:4) and ligated into the vaccinia virus transfer vector PT116. This vector contains a strong vaccinia virus immediate early promoter (designated P40) upstream of the multiple cloning site to drive the synthesis of the inserted gene product. The ligation and orientation of the B7 DNA fragments, as well as promoter position were verified by PCR and sequencing. The chimeric vector construct was inserted into the vaccinia virus genomic Hind III M site by homologous recombination as previously reported (Kaufman H. et al. *Int. J. Cancer* 48:900-907, 1991), and confirmed by Southern analyses with $^{32}$P radiolabeled B7-1 or B7-2 DNA as a probe (data not shown). The entire cDNA sequences of B7-1 and B7-2 in the vaccinia virus clones were shown to be identical to the published sequences (Freeman, G. J. et al. *J. Exp. Med.* 174:625-631, 1991; Freeman, G. J. et al. *Science* 262:813-960; 1993).

Expression of recombinant protein was confirmed by western analysis of protein extracts from rV-B7-1 or rV-B7-2 infected BSC-1 cells. These cells are routinely used for the evaluation of recombinant vaccinia products (Moss, B. Current Protocols in Molecular Biology 2.16.15.1-16.18.9, 1993). Incubation of protein extract blots from rV-B7-1 infected cells with the rat anti-mouse monoclonal antibody B7-BB1 revealed a broad 50-90 kD band. Similarly, incubation of protein extract blots from rV-B7-2 infected cells with the rat anti-mouse monoclonal antibody B7-2 (GL-1) revealed a band ranging from 65-100 kD (data not shown). This is consistent with reports indicating the apparent molecular mass of these molecules, which appear as glycoproteins that are heterogeneous as a result of N-linked glycosylation (Schwartz, R. H. *Cell* 71:1065-1068, 1992; Freeman, G. J. et al. *J. Exp. Med.* 174:625-631, 1991; Freeman, G. J. et al. *Science* 262:813-960, 1993). Uninfected or V-Wyeth infected cells were negative for the expression of both B7-1 and B7-2.

Figure 1B:
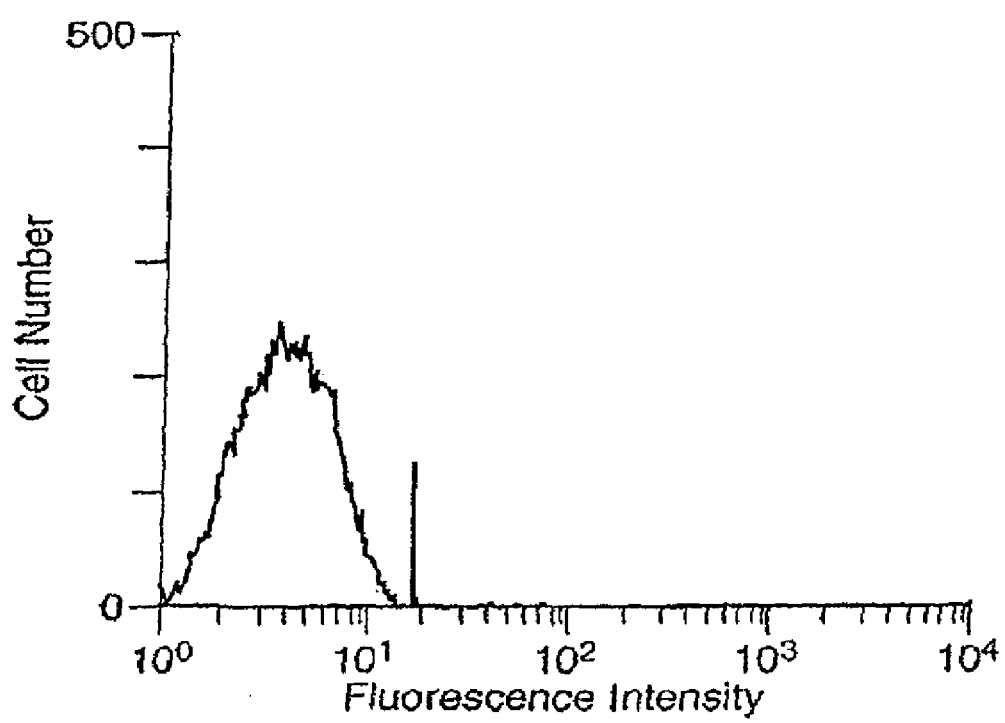
Figure 1C:
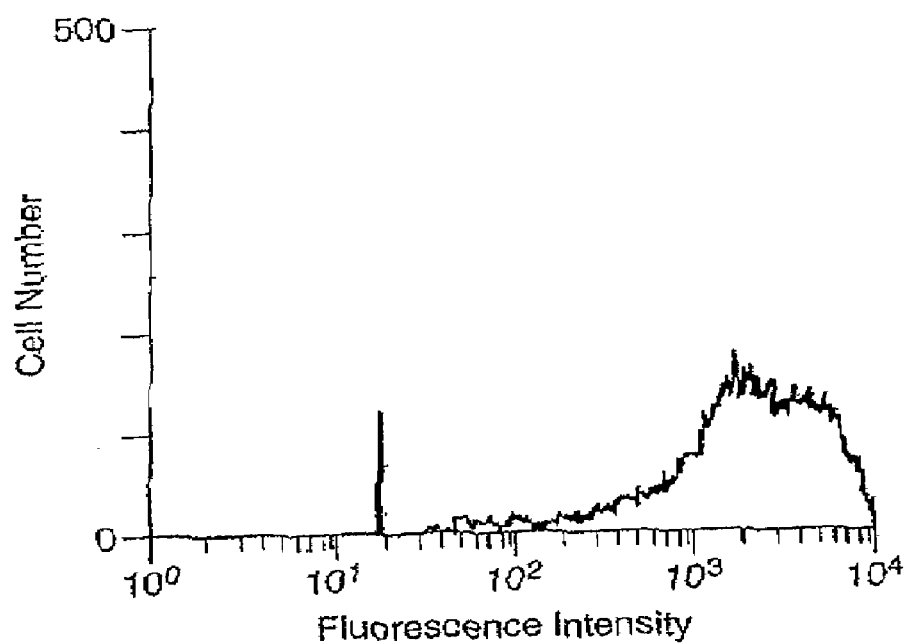
Figure 1D:
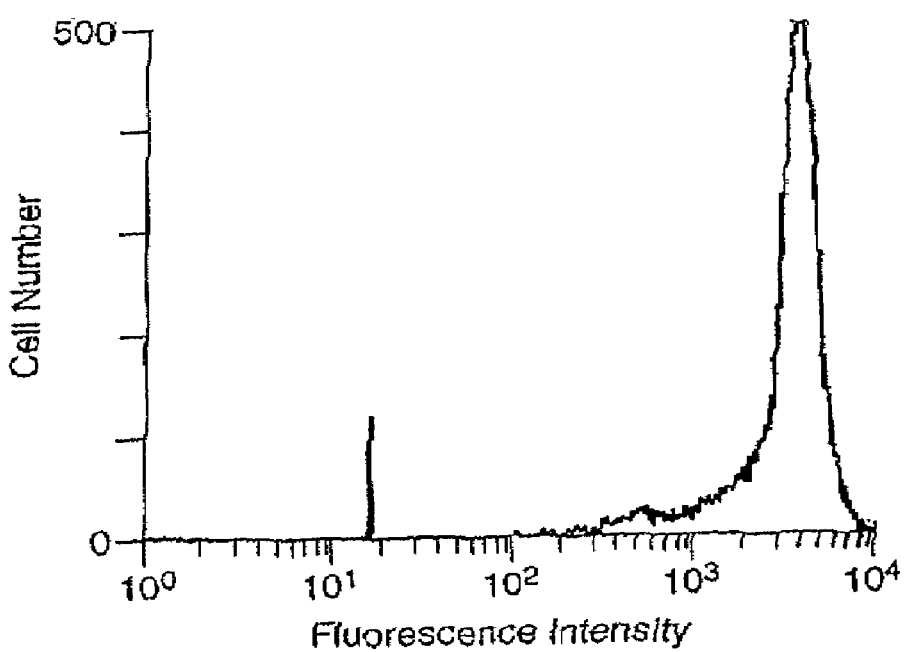
Figure 2A:
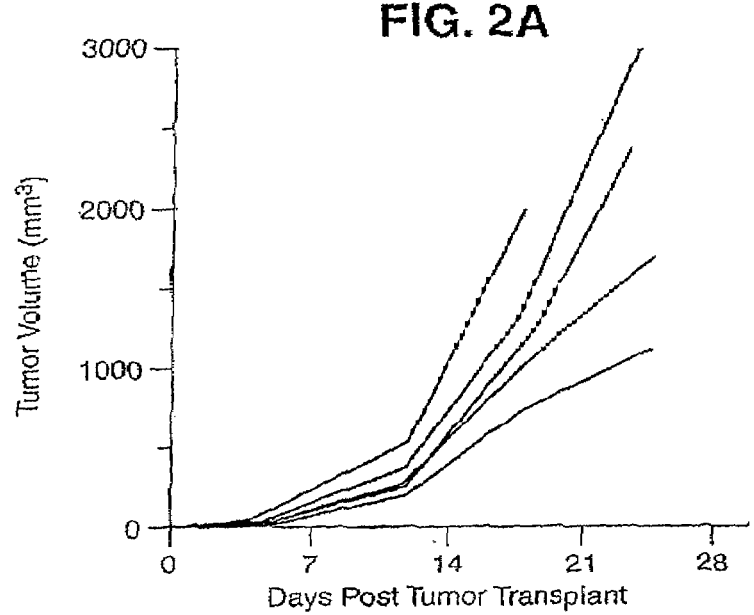
FIGS. 2A-2D shows growth of transplanted mouse adenocarcinoma cells expressing rV-B7 proteins. Five C57BL/6 mice per group were injected with $3 \times 10^5$ MC38 cells that were uninfected (FIG. 2A), infected with 0.25 MOI V-Wyeth (FIG. 2B), rV-B7-1 (FIG. 2C), or rV-B7-2 (FIG. 2D).
Figure 2B:
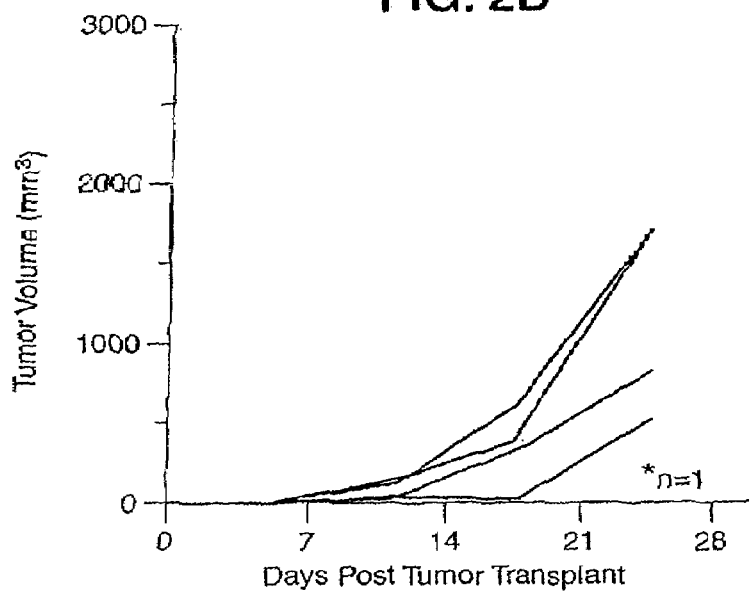
Figure 2C:
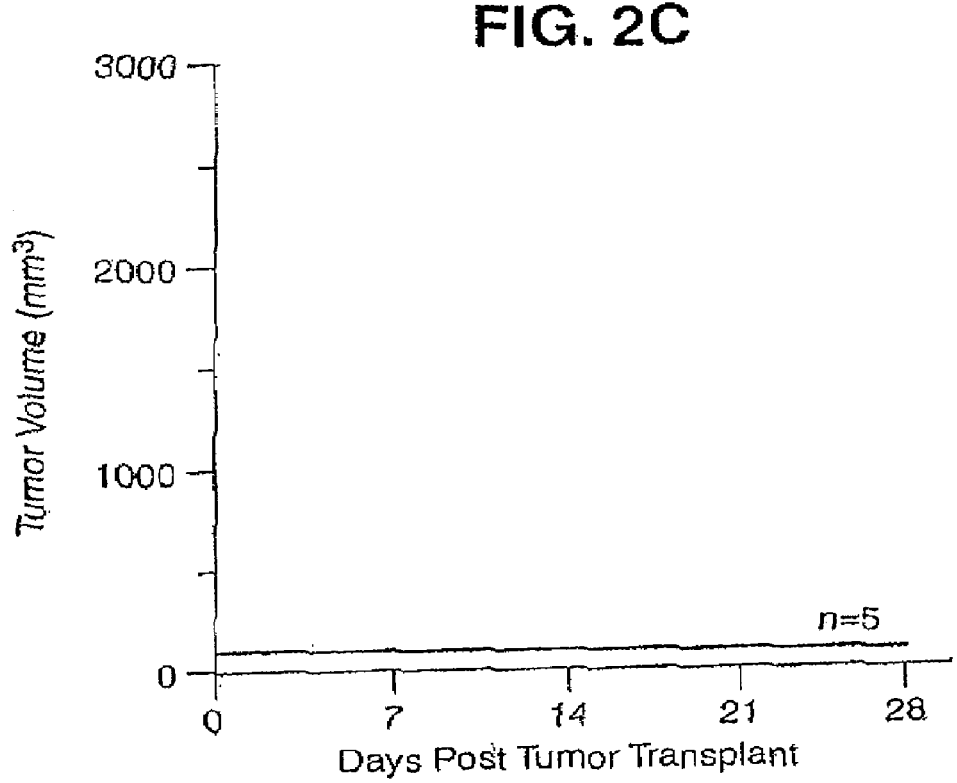
Figure 2D:
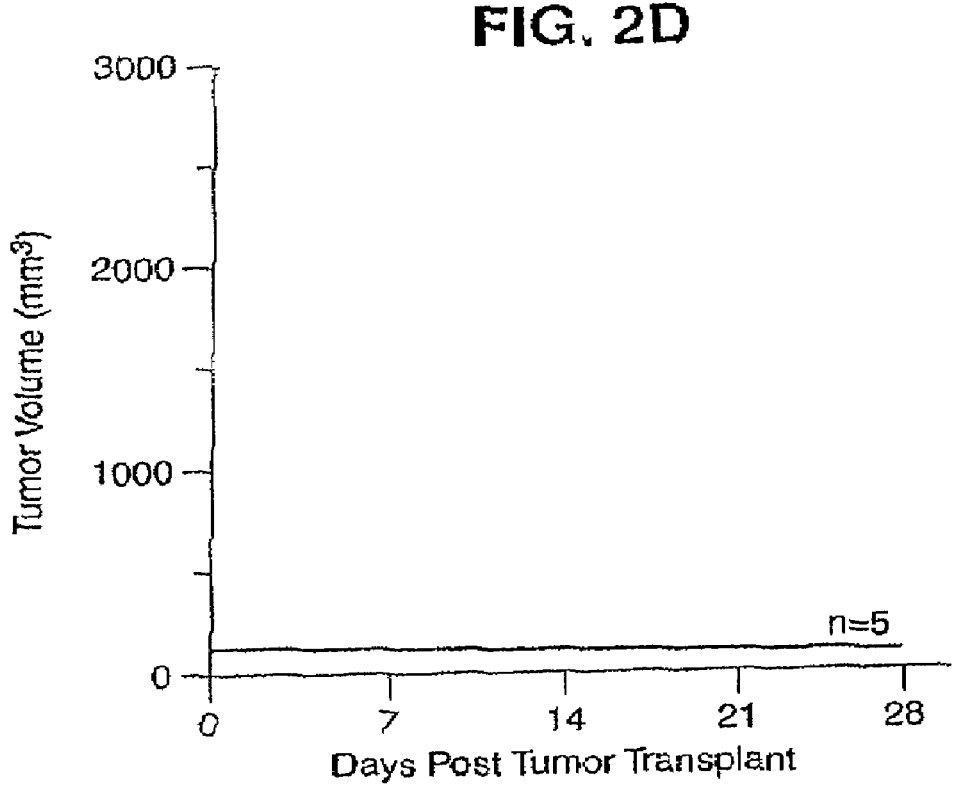

Cell surface expression of B7-1 or B7-2 recombinant proteins was examined by flow cytometry. FIG. 1A illustrates that uninfected BSC-1 cells (FIG. 1A) do not react with either B7(BB1) or B7-2 (G1-1) antibodies (98.5% of the cells are negative with a mean fluorescence of 5.22). Similarly, cells infected with wild type vaccinia (V-Wyeth, FIG. 1B), failed to react with either of these two antibodies (97.7% of the cells are negative with a mean fluorescence of 5.43). BSC-1 cells infected with rV-B7-1 (FIG. 1C) react strongly with the B7/BB1 antibody (97.5% of the cells are positive with a mean fluorescence of 2513.68). Cells infected with rV-B7-2 (FIG. 1D) react strongly with the B7-2 (G1-1) antibody (98.8% of the cells are positive with a mean fluorescence of 1802.30). There was no reactivity between antibody B7/BB1 and cells infected with rV-B7-2, and no reactivity of antibody GL-1 with cells infected with rv-B7-1. These studies thus demonstrate that a recombinant vaccinia virus can express the B7-1 and B7-2 molecules on the cell surface at 3-6 hours post infection. Lysis of infected cells usually does not occur for 24-48 hours (Moss, B. Current Protocols in Molecular Biology 2.16.15.1-16.18.9, 1993).

It has previously been shown that the injection of $3 \times 10^5$ MC38 murine adenocarcinoma cells subcutaneously into syngeneic C57BL/6 routinely gives rise to palpable tumors within 7 to 14 days followed by rapid growth that is ultimately fatal (Kantor, J. et al. *J. Nat'l Cancer Inst.* 84:1084-1091, 1992). These tumor cells have also been shown to be negative for the expression of B7 (Chen, L. et al. *J. Exp. Med.* 179: 523-532, 1992). To test the recombinant vaccinia constructs for the functional expression of B7, the growth of MC38 tumor cells was compared to that of MC38 infected with rV-B7-1, rV-B7-2, and wild type V-Wyeth (FIGS. 2A-2D). The injection of uninfected MC38 cells (FIG. 2A) resulted in palpable tumors in all animals within 7 days. Tumor growth was progressive throughout the duration of this experiment. Animals were killed in all experiments when any tumor measurement (length or width) exceeded 20 mm. The injection of MC38 cells infected for 1 hour with 0.25 MOI V-Wyeth (FIG. 2B) resulted in a slight delay of onset of palpable tumor, and all animals eventually became positive for tumor (one animal in FIG. 2B grew an intraperitoneal tumor which could not be measured). The MOI of 0.25 was chosen for all groups because infections with greater than that amount resulted in higher levels of non-specific cell death resulting in slower tumor growth. The injection of MC38 cells infected with 0.25 MOI of rV-B7-1 (FIG. 2C) or rV-B7-2 (FIG. 2D) failed to induce tumors in any mice, which remained tumor free for the duration of this experiment.

Recombinant protein expression of cells infected as this MOI was confirmed by flow cytometry. After infection with 0.25 MOI recombinant virus, approximately 35% of MC38 cells were positive for either recombinant B7-1 or B7-2 with an average mean fluorescence ranging from 417-585. MC38 cells either uninfected or infected with 0.25 MOI V-Wyeth remained negative for expression of B7-1 or B7-2. These MC38 cells were positive for the expression of Class I MHC antigen both before and after infection. No gross toxic effects were observed in any of these animals during the 40 day observation panel. Animal weights remained within one standard deviation of normal age-matched mice. These experiments were repeated 3 additional times with similar results.

Studies were conducted to determine whether tumor rejection is dependent on an intact immune system. In these studies, mice were immunosuppressed by radiation (see materials and methods Example 1) and were administered infected MC38 tumor cells (Table 1). Tumors in irradiated mice infected with V-Wyeth, rV-B7-1 or rV-B7-2 were measurable 14 days after tumor transplant and no difference in tumor volumes were observed, indicating that an intact immune system is necessary to respond to the recombinant B7 molecules.

TABLE 1

Growth of Infected MC38 Tumor In Irradiated Mice (14 Days post tumor transplant)

| Infection | # Of Animals With Tumor | Mean Tumor Volume (MM$^3$ ± SEM) |
| --- | --- | --- |
| MC38 (Wyeth) | 5/5 | 369.9 ± 141.8 |
| MC38 (rV-B7-1) | 5/5 | 441.9 ± 204.2 |
| MC38 (rV-B7-2) | 5/5 | 404.0 ± 237.3 |

Growth of MC38 tumors in immunocompromised animals. Mice were gamma irradiated and injected with MC38 cells that had been infected for 1 hour with 0.25 MOI of either V-Wyeth, rV-B7-1, or rV-B7-2.

Figure 3A:
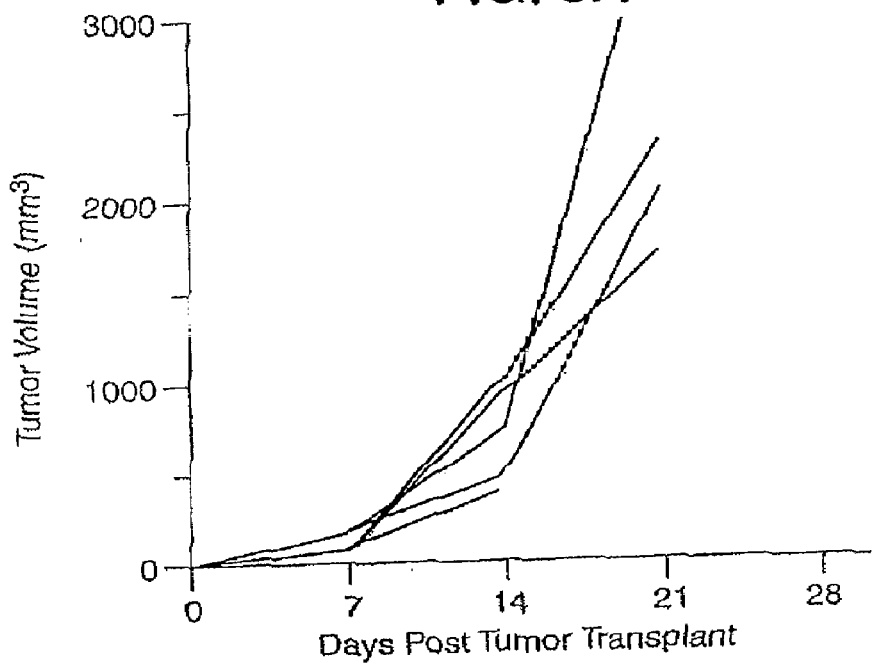
FIGS. 3A-3C.
Figure 3B:
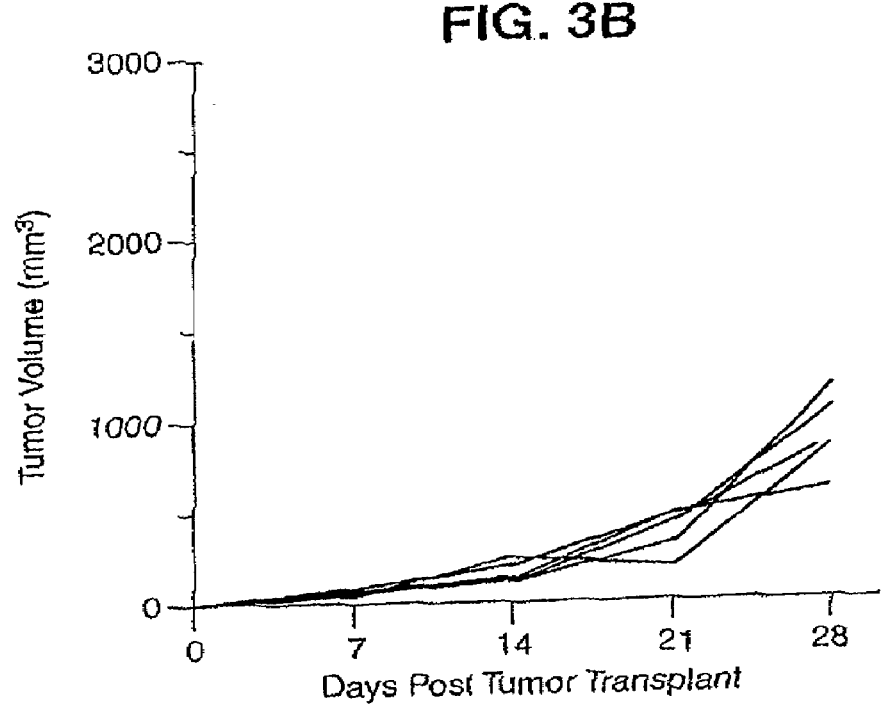
Figure 3C:
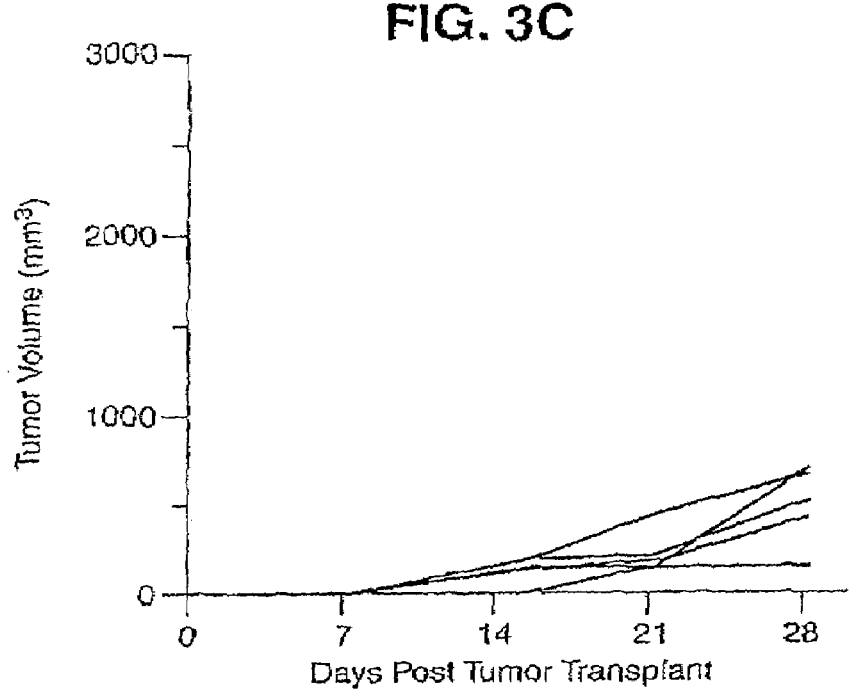

In systems using retroviral vectors for introduction of B7 genes, it has been shown that concurrent administration to mice of B7 expressing tumor cells on one flank and administration of B7 negative tumor cells on the opposite flank would prevent the growth of both tumor populations (Chen, L. et al. *Cell* 71:1093-1102, 1992). In other studies, antitumor activity to B7 negative cells was demonstrated by the multiple intraperitoneal injections of B7 expressing tumor cells ten days following the subcutaneous administration of B7 negative primary tumor (Li, Y. et al. *J. Immunol* 153:421-428, 1994). The study described here was designed to determine if long lasting immunity to tumor cells could be induced by immunization with rV-B7 infected tumor cells. Mice administered MC38 cells infected with rV-B7-1 or rV-B7-2 remained tumor free for in at least 40 days (FIGS. 2C and 2D) and were then challenged on the opposite flank with $3 \times 10^5$ uninfected (B7 negative) MC38 cells (FIGS. 3B and 3C). The injection of these MC38 cells into naive mice (FIG. 3A) resulted in palpable tumor formation in all animals within 7 days, with progressive tumor growth throughout the duration of this experiment. Average tumor volume in this control group at 21 days post tumor transplant was 2436±858 mm$^3$. Mice that had 40 days previously been administered tumor infected with rV-B7-1 were also challenged with uninfected MC38 cells (FIG. 3B). The formation of these tumors was delayed, and the growth rate was substantially reduced, with an average tumor volume of 372±106 mm$^3$ at day 21. Similarly, mice that had been administered rV-B7-2 infected tumors, when challenged with MC38 cells, displayed a substantial reduction in growth of tumor cells. Average tumor volume in this group was 197±161 mm$^3$ at day 21. Tumor growth was thus reduced by >90% in animals previously receiving tumors expressing B7-1 or B7-2 via recombinant vaccinia virus infection. This was of interest in light of the fact that only one immunization was administered 40 days prior to tumor challenge, and that the mice were challenged with a relatively large tumor burden. This implies that a memory immune response against a rejection antigen on MC38 tumor cells is being induced by the injection of rV-B7 infected tumor cells. The above method of treatment may be modified to include multiple inoculations with B7 expressing tumor cells, and enhancement of T-cell activation with immunostimulatory molecules including cytokines such as IL-2.

Previous studies have demonstrated that the introduction of B7 into tumor cells via transduction with retroviral vectors such as PLNSX, PLNCX or PLXSN can confer immunogenicity to those tumors (Chen, L. et al. *J. Exp. Med.* 179:523-532, 1994; Dohring, C. et al. *Int. J. Cancer* 57:754-759, 1994). These methods of B7 introduction have a potential limitation for clinical applications due to a relatively low efficiency of infection of retroviral vectors and the consequent prolonged amount of time required to drug select and expand the B7 positive tumor cells. As an alternative, the studies reported here have demonstrated the development of recombinant vaccinia viruses expressing the genes for the costimulatory molecules B7-1 and B7-2. These recombinant vaccinia constructs infect tumor cells rapidly (14 hours) and express recombinant protein with high efficiency (over 97% of cells, FIGS. 1C and 1D, respectively). Infected cells were shown to authentically synthesize the recombinant proteins, leading to antitumor effects. These studies thus present data in an experimental system for the insertion of B7 genes into vaccinia virus vectors with implications for potential immunotherapeutic applications.

EXAMPLE 3

Induction of Enhanced a T-Cell Immune Response to a Human Tumor Associated Antigen by Mixing a Recombinant Vaccinia Virus Expressing the Tumor Associated Antigen with a Recombinant Vaccinia Virus Expressing the B7 Co-Stimulatory Molecule The present invention comprises a composition of rV-B7 in combination with a recombinant vaccinia virus expressing a human tumor associated antigen. The composition of the present invention when coinoculated into a host to enhance the systemic T-cell immune response to that human tumor associated antigen.

Several human tumor associated antigens have now been identified. One of these is the human carcinoembryonic antigen (CEA) which is expressed on a range of human carcinomas including colorectal, gastric, pancreatic, breast and non-small cell lung cancers. It have previously been shown that a recombinant vaccinia CEA construct designated rV-CEA can be administered to both mice and rhesus monkeys and induce T-cell responses specific for CEA in both model systems (Kantor J. et al., J. Natl. Cancer Ins. 84:1084-1091, 1992; Kantor J. et al., Cancer Res. 52:6917-6925, 1992). Moreover, no toxicity was observed in either system. Recently, a clinical trial has been completed in which rV-CEA was administered to patients with metastatic gastrointestinal, breast or lung carcinomas. In this Phase I study, no toxicity other than one would observe with administration of the smallpox vaccine was observed.

One embodiment is the insertion of the B7 and CEA genes into the same recombinant vaccinia construct since both molecules need to be expressed on the same cell at the same time. Another embodiment is the mixing a rV-CEA with a rV-B7 to specifically enhance the T-cell immune response to CEA. The advantages of this latter approach, is several fold: (a) different ratios of rV-CEA and rV-B7 can be tested to determine the ratio for an optimal immune response, (b) the timing of administration of rV-CEA and rV-B7 can be altered, (c) only one rV-B7 construct needs to be manufactured, i.e., the rV-B7 employed with rV-CEA can also be used with a rV construct to other tumor associated antigens and indeed any other antigen associated with a disease agent for enhancement of an immune response.

In one embodiment, it was demonstrated that simply mixing rV-CEA with rV-B7 and coadministration to the host led to an enhanced T-cell immune response specific for CEA. Moreover, the ratios of rV-CEA to rV-B7 were important factors in the magnitude of the immune response.

Figure 4:
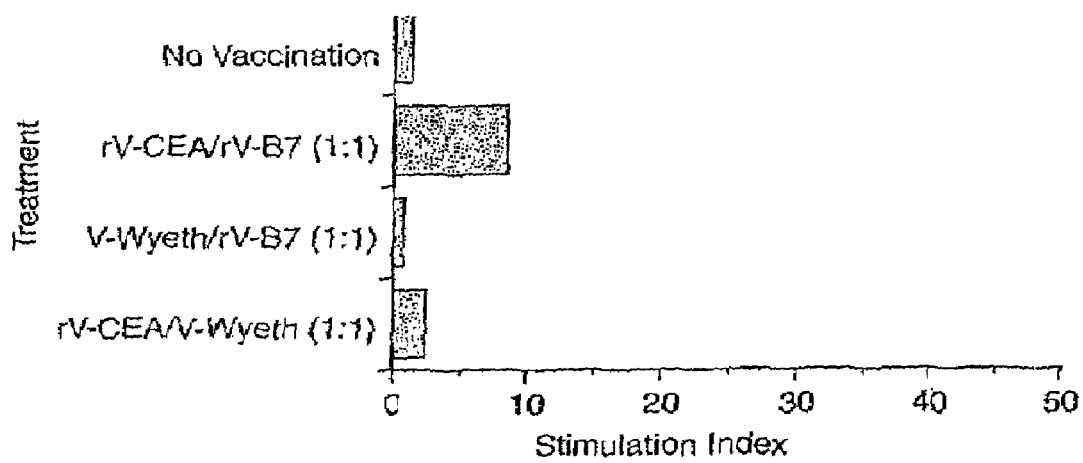
FIG. 4 shows each treatment group of 5 C57BL/6 mice immunized with recombinant vaccinia viruses encoding the genes for either human carcinoembryonic antigen gene (rV-CEA), murine B7-2 (rV-B7), or the wild type strain of vaccinia virus (V-Wyeth). Each mouse was administered $1 \times 10^7$ plaque forming units by tail scarification in the following ratios: 1:1 rV-CEA/rV-B7 ($5 \times 10^6$ PFU rV-CEA+$5 \times 10^6$ PFU rV-B7); 1:1 V-Wyeth/rV-B7 ($5 \times 10^6$ PFU V-Wyeth+$5 \times 10^6$ PFU rV-B7); or 1:1 rV-CEA/V-Wyeth ($5 \times 10^6$ PFU rV-CEA+$5 \times 10^6$ PFU V-Wyeth). Three spleens were removed and pooled from each treatment group 14 days after immunization and a standard 5 day lymphoproliferative assay was performed as previously described (Kantor, et al. *JNCI*, 84:1084, 1992). Purified T cells were tested for their proliferative capacity against a Baculovirus produced recombinant CEA at 100 μg/ml. Stimulation index was calculated in relationship to the cells reactivity to media (background).

In the first study, rV-CEA and rV-B7 were mixed at one to one ratios, i.e., $5 \times 10^6$ pfu of B7 and $5 \times 10^6$ pfu of rV-CEA were mixed and coadministered to groups of three mice by tail scarification. Spleens were removed 14 days post-immunization as a source of lymphocytes. As controls, three other groups of mice were used: (a) non-vaccinated mice, (b) mice receiving $5 \times 10^6$ pfu of rV-CEA and $5 \times 10^6$ pfu of wild type vaccinia (designated V-Wyeth), and (c) mice receiving $5 \times 10^6$ pfu of V-Wyeth and $5 \times 10^6$ pfu of rV-B7. Thus, all vaccinated mice received a total of $10^7$ pfu of vaccinia virus and in all three groups, ratios of vaccinia viruses were 1 to 1. As can be seen in FIG. 4, after one administration of rV-CEA plus V-Wyeth, mice did mount an immune response specific for CEA, albeit low. The immune assay employed was a lymphoproliferative assay which as been described previously (Kantor et al., *J. Natl. Cancer Inst.*, 84:1084-1092, 1992) and the target antigen used was recombinant CEA derived from baculovirus. As can be seen in FIG. 4, the addition of rV-B7 to rV-CEA enhanced the specific immune response several fold. In contrast, the addition of rV-B7 to the control V-Wyeth had no effect on enhancing the CEA specific immune response.

Figure 5:
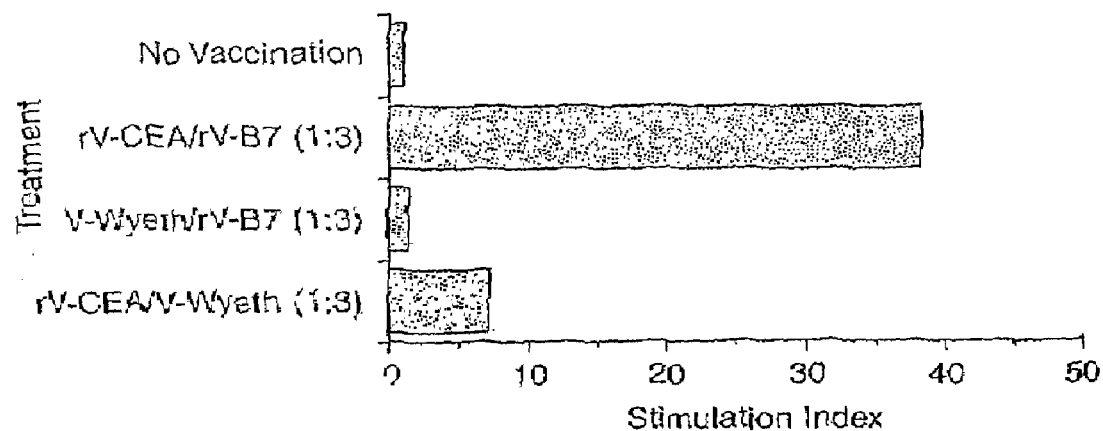
FIG. 5 shows each treatment group of 5 C57BL/6 mice immunized with recombinant vaccinia viruses encoding the genes for either human carcinoembryonic antigen gene (rV-CEA), murine B7-2 (rV-B7), or the wild type strain of vaccinia virus (V-Wyeth). Each mouse was administered $1 \times 10^7$ plaque forming units by tail scarification in the following ratios: 1:3 rV-CEA/rV-B7 ($2.5 \times 10^6$ PFU rV-CEA+$7.5 \times 10^6$ PFU rV-B7); 1:3 V-Wyeth/rV-B7 ($2.5 \times 10^6$ PFU V-Wyeth+$7.5 \times 10^6$ PFU rV-B7); or 1:3 rV-CEA/V-Wyeth ($2.5 \times 10^6$ PFU rV-CEA+$7.5 \times 10^6$ PFU V-Wyeth). Three spleens were removed and pooled 14 days after immunization and a standard 5 day lymphoproliferative assay was performed as previously described (Kantor, et al. *JNCI*, 84:1084, 1992). Purified T-ells were tested for their proliferative capacity against a Baculovirus produced recombinant CEA at 100μ/ml. Stimulation index was calculated in relationship to the cells reactivity to media (background).

In the next study the ratio of rV-CEA to rV-B7 was modified to that of 1 to 3. As shown in FIG. 5, the administration of rV-CEA plus rV-B7 at the 1:3 ratio enhanced the CEA specific T-cell response as compared to rV-CEA plus V-Wyeth, and to a greater extent than when the two constructs (rV-B7 plus rV-CEA) were mixed at a 1:1 ratio. Again, the two control groups, i.e., no vaccination and rV-B7 mixed with V-Wyeth showed no immune response to CEA.

These results indicate that simply mixing a rV-containing a human associated gene with rV-B7 can lead to coinfection and coexpression on antigen presenting cells so as to enhance specific T-cell responses for the human tumor associated antigen. Moreover, it appears that the ratios of rV-B7 and the rV-containing human associated gene used may be an important factor in optimizing T-cell activation to a human tumor associated gene product or indeed any other gene product one wished to induce or enhance immunity to.

EXAMPLE 4

Lymphoproliferative Responses of Mouse T-cells to CEA after Immunization with rV-CEA+rV-B7

Lymphoproliferative Responses:

C57BL/6 mice were immunized with $1 \times 10^7$ PFU total virus with various ratios of either: V-Wyeth; rV-CEA:V-Wyeth; Wyeth:rV-B7; or rV-CEA:rV-B7, and CEA specific lymphoproliferation was analyzed as previously described (Kantor, J. et al *J. Nat'l Cancer Inst.* 84:1084-1091, 1992). Briefly, spleens were removed 14 days following immunization and mechanically dispersed through 70 μm cell strainers (Falcon, Becton Dickinson, Franklin Lakes, N.J.) to isolate single cell suspensions. Erythrocytes and dead cells were removed by centrifugation over a Ficoll-Hypaque gradient (density=1.119 g/ml) (Sigma Chemical Co., St. Louis, Mo.). Populations consisting of approximately 95% T-cells were obtained by passage of splenic mononuclear cells over nylon wool columns (Robbins Scientific Corp., Sunnyvale, Calif.). To evaluate CEA specific lymphoproliferation, T-cells were added at $10^5$/well in 96 well flat bottomed plates (Costar, Cambridge, Mass.). Antigen presenting cells consisted of irradiated (2000 rads) naive syngeneic splenocytes added at $5 \times 10^5$/well. Stimulated wells received purified human CEA (100-12.5 μg/ml) (Vitro Diagnostics, Denver, Colo.); ovalbumin as a negative control (100 μg/ml); UV-inactivated V-Wyeth (2×10$^7$ PFU/ml) as a recall antigen or Con-A (2 μg/ml) as a T-cell positive control. Control wells received T-cells, APC's and media only. Cells in all wells were cultured in a total volume of 200 μl of complete media (CM), [RPMI 1640 with fetal calf serum (10%); glutamine (2 mM), sodium pyruvate (1 mM), Hepes (7 mM), gentamicin (50 μg/ml), 2-mercaptoethanol (50 μM), and non-essential amino acids (0.1 mM), (Biofluids, Rockville, Md.)] for 5 days. Cells were labeled for the final 12-18 h of the incubation with 1 μCi/well [$^3$H]thymidine (New England Nuclear, Wilmington, Del.) and harvested with a PHD cell harvester (Cambridge Technology, Cambridge, Mass.). The incorporated radioactivity was measured by liquid scintillation counting (LS 6000IC; Beckman, Duarte, Calif.). The results from triplicate wells were averaged and are reported as stimulation index (SI) as calculated: SI=[CPM (stimulated wells)]/[CPM (control wells)].

Lymphoproliferative Analysis:

To determine if immunization with an admixture of rV-CEA and rV-B7 could result in enhanced CEA specific lymphoproliferative responses, C57BL/6 mice were immunized one time with a total of 10$^7$ PFU of rV-CEA:V-Wyeth, V-Wyeth:rV-B7, or rV-CEA:rV-B7, at either 1:1, 1:3, or 3:1 ratios (see Table 2) and lymphoproliferative responses were analyzed after 14 days. Table 2 shows that T-cells from mice receiving no immunization failed to respond to purified CEA, while T-cells from mice immunized with rV-CEA:V-Wyeth responded weakly (stimulation index [SI] of 1.9-2.5). The response to CEA appeared to be related to the dose of rV-CEA given during the immunization. T-cells from mice immunized with all ratios of V-Wyeth:rV-B7 failed to respond to CEA. In contrast, T-cells from mice immunized with any ratio of rV-CEA:rV-B7 appeared to have an increased response to CEA in comparison to the cohorts receiving no rV-B7 with their immunization (Table 2). The immunization of rV-CEA:rV-B7 (3:1) was optimal for induction of lymphoproliferation in this experiment (SI of 12.3). Experiment in which rV-CEA:rV-B7 ratios were altered (3:1, 1:1, 1:3) were conducted 4 times, and in each case the 3:1 ratio provided the greatest increase in CEA specific T-cell responses. To further examine the extent of the CEA specific cellular immune response, mice were immunized one time with rV-CEA:V-Wyeth (3:1); V-Wyeth:rV-B7 (3:1); or rV-CEA:rV-B7 (3:1) and lymphoproliferative responses were analyzed as before.

TABLE 2

Lymphoproliferative Responses of Mouse T-cells to CEA after Immunization with Various Ratios of rV-CEA + rV-B7

| Immunogen$^a$ | Ratio (1 × 10$^7$ total) | Antigen$^b$ Con A | Oval | CEA |
|---|---|---|---|---|
| No Immunization | NA$^c$ | 359 | 1.0 | 1.4 |
| rV-CEA/V-Wyeth | 1:1 | 312 | 1.7 | 2.1 |
| rV-CEA/V-Wyeth | 1:3 | 284 | 0.9 | 1.9 |
| rV-CEA/V-Wyeth | 3:1 | 442 | 1.0 | 2.5 |
| V-Wyeth/rV-B7 | 1:1 | 359 | 1.0 | 1.7 |
| V-Wyeth/rV-B7 | 1:3 | 412 | 1.9 | 1.6 |
| V-Wyeth/rV-B7 | 3:1 | 387 | 1.8 | 0.4 |
| rV-CEA/rV-B7 | 1:1 | 403 | 1.4 | 7.0$^d$ |
| rV-CEA/rV-B7 | 1:3 | 394 | 1.0 | 4.0 |
| rV-CEA/rV-B7 | 3:1 | 345 | 1.8 | 12.3 |

$^a$5 C57BL/6 mice were immunized one time as indicated. Lymphoproliferative responses from pooled splenic T-cells were analyzed 14 days following immunization.
$^b$Antigen concentrations were: Con A (2 μg/ml); ovalbumin (100 μg/ml); and CEA (100 μg/ml). Each value represents the stimulation index of the mean CPM of triplicate samples versus media. Standard deviation never exceeded 10%.
$^c$NA, Not applicable.
$^d$Values in bold are significant when compared to their respective medium control values (p < 0.001).

Table 3 shows that T-cells from mice receiving no immunization failed to respond to purified CEA at any concentration, or to UV-inactivated V-Wyeth. T-cells from mice immunized with V-Wyeth responded to UV-V-Wyeth with a strong stimulation index (31.7), while failing to proliferate in response to CEA. In contrast, T-cells from mice immunized with rV-CEA:V-Wyeth (3:1) proliferated when cultured with CEA in a dose dependent manner (stimulation index of 4.5-1.6). T-cells from mice immunized only with rV-B7 (Y-Wyeth:rV-B7) failed to respond to CEA. Finally, T-cells from mice immunized with the combination of rV-CEA and rV-B7 (3:1) proliferated in response to CEA antigen in a dose dependent manner (SI=18.6-3.0). This stimulation index represents a greater than 4-fold increase in CEA specific proliferative responses following the addition of rV-B7. T-cells from every group responded to the control lymphocyte mitogen Con A, and failed to react with the negative control antigen ovalbumin.

TABLE 3

Lymphoproliferative Responses of Mouse T-cells to CEA after Immunization with 3:1 Ratio of rV-CEA+rV-B7

| Immunogen$^a$ | Ratio (1 × 10$^7$ total) | Con A | Oval | UV V-Wyeth | CEA (μg/ml) 100 | 50 | 25 | 12.5 |
|---|---|---|---|---|---|---|---|---|
| No Immunization | NA$^c$ | 456 | 1.0 | 1.1 | 2.2 | 1.4 | 0.9 | 0.6 |
| V-Wyeth/V-Wyeth | NA | 471 | 1.7 | 31.7 | 2.2 | 2.8 | 2.2 | 1.9 |
| rV-CEA/V-Wyeth | 3:1 | 451 | 1.0 | 35.4 | 4.5 | 3.6 | 2.5 | 1.6 |

TABLE 3-continued

Lymphoproliferative Responses of Mouse T-cells to CEA after
Immunization with 3:1 Ratio of rV-CEA+rV-B7

| | Ratio | | | Antigen[b] | | | | |
|---|---|---|---|---|---|---|---|---|
| | (1 × 10[7] | | | UV | CEA (µg/ml) | | | |
| Immunogen[a] | total) | Con A | Oval | V-Wyeth | 100 | 50 | 25 | 12.5 |
| V-Wyeth/rV-B7 | 3:1 | 345 | 1.8 | 42.0 | 1.4 | 0.4 | 0.0 | 0.0 |
| rV-CEA/rV-B7 | 3:1 | 395 | 1.9 | 40 | 18.6[d] | 7.2 | 6.5 | 3.0 |

[a]5 C57BL/6 mice were immunized one time as indicated. Lymphoproliferative responses from pooled splenic T-cells were analyzed 14 days following immunization.
[b]Antigen concentrations were: Con A (2 µg/ml); Ovalbumin (100 µg/ml); UV-Wyeth (2 × 10[7] pfu/ml); and CEA (100-12.5 µg/ml). Each value represents the stimulation index of the mean CPM of triplicate samples versus media. Standard deviation never exceeded 10%.
[c]NA, Not applicable.
[d]Values in bold are significant when compared to their respective medium control values (p < 0.001).

EXAMPLE 5

Dual Expression of Both CEA and B7-1 on Cells Infected with rV-CEA and rV-B7

Flow Cytometry Methods

Two color flow cytometry was used to demonstrate dual infection of cells in-vitro with rV-CEA and rV-B7. Confluent BSC-1 cells (CCI 26, ATCC, Rockville, Md.) were infected for 2 hours with a 3:1 mixture of either rV-CEA:rV-B7, rV-CEA:V-Wyeth, V-Wyeth:rV-B7, or V-Wyeth alone, at a total MOI of 5. Cells were harvested 18 h post infection and stained with a combination of PE-conjugated rat anti-mouse B7-1 mAb (Pharmingen, San Diego, Calif.) and FITC-conjugated anti-CEA mAb COL-1 (36) or FITC- and PE-conjugated isotype-matched control mAb (Pharmingen). The COL-1 mAb was conjugated to FITC using a standard method (37). Cell fluorescence was analyzed by using a FACSCAN (Becton Dickinson, Mountain View, Calif.) with the Lysis II software.

Flow Cytometric Analysis: Dual Expression of Recombinant CEA and B7

Figure 6D:
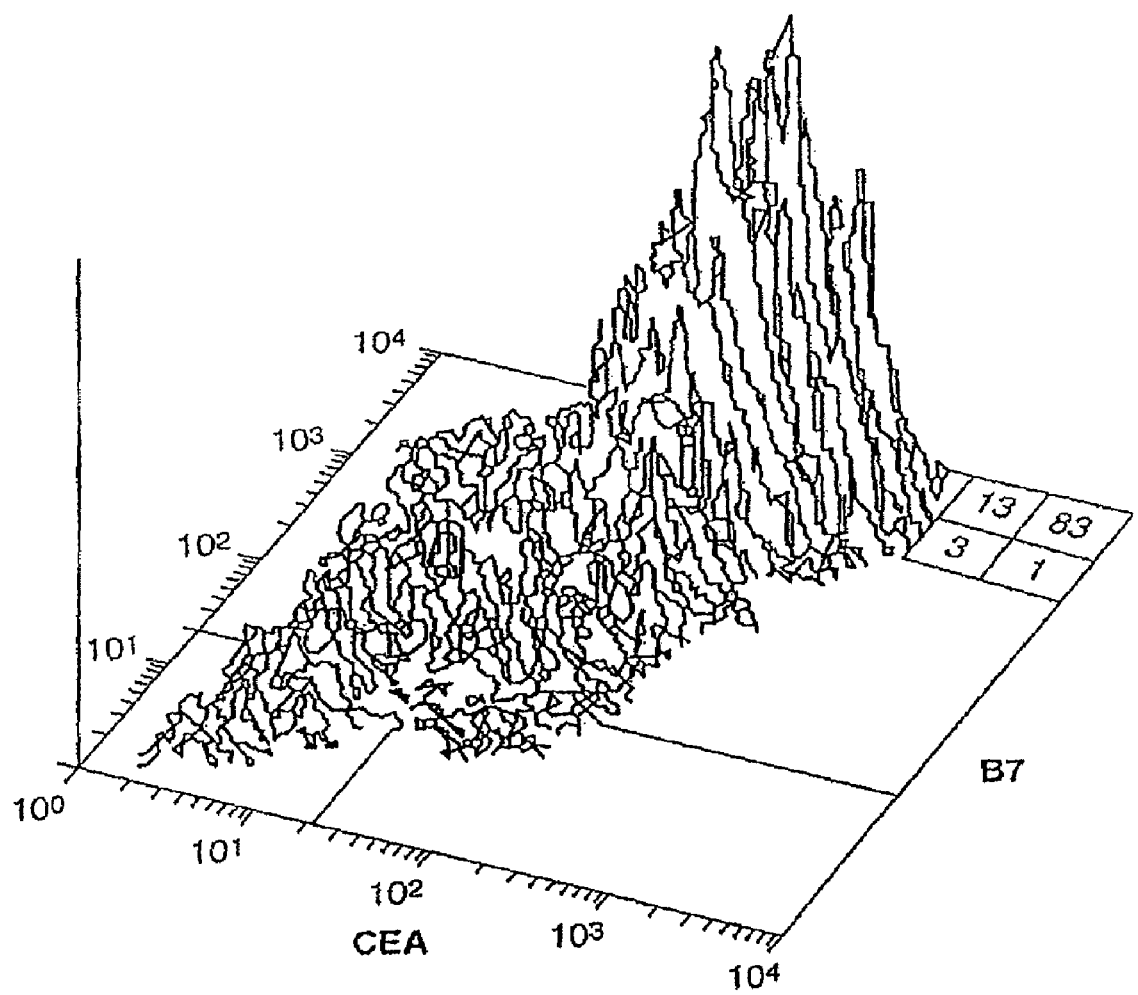

Because it has been proposed that both antigen and B7-1 must be expressed in close proximity to each other to properly co-engage the T-cell and CD28 receptors (Jenkins, M. K. et al *Current Opinion in Immunol.* 5:361-367, 1993; Hathcock, K. S. et al *J. Exp. Med.* 180:631-640, 1994; Hellstrom, K. E. et al *Ann. NY Acad. Sci.* 690:225-230, 1993: Harding, F. A. et al *J. Exp. Med.* 177:1791-1796, 1993), it was determined whether infection of cells with a mixture of rV-CEA and rV-B7 would lead to dual expression of both CEA and B7-1 on the cell surface. To determine dual expression, BSC-1 cells were infected with a 3:1 mixture of rV-CEA:V-Wyeth, V-Wyeth:rV-B7, or rV-CEA:rV-B7 or V-Wyeth alone, and analyzed by two color flow cytometry. Cells infected with V-Wyeth:V-Wyeth demonstrated only background levels of staining (FIG. 6A); whereas cells infected with rV-CEA:V-Wyeth were positive principally for CEA (FIG. 6B). Similarly, cells infected with the mixture of V-Wyeth:rV-B7 were positive principally for B7-1 (FIG. 6C). Cells co-infected with rV-CEA:rV-B7, however, were positive for both CEA and B7-1 (FIG. 6D).

EXAMPLE 6

Increased CEA Specific Cytotoxicity following Immunization with rV-CEA:rV-B7

Cytolytic Response Methods:

Mice were immunized as described in Example 4 and CEA specific cytolytic activity was analyzed as previously described (Kantor, J. et al *J. Nat'l Cancer Insti.* 84:1084-1091, 1992). Briefly, spleens were removed 14 days following immunization, dispersed into single cell suspensions, and run over Ficoll-Hypaque gradients. The MC38 murine colonic adenocarcinoma cell line (Fox, B. A. et al *J. Bio. Resp. Modifiers* 9:499-511, 1990) was supplied by the laboratory of Dr. Steve Rosenberg (National Cancer Institute, Bethesda, Md.). The derivative cell line expressing human CEA, MC-38-CEA-2, has been described (Robbins, P. F. et al *Cancer Res.* 51:3657-3662, 1991). These tumor cells were prepared for use as targets in a standard cytolytic assay (Wunderlich, J. et al *Current Protocols in Immunology*, Colligan, J. E. et al (eds) 3.11.1-3.11.14, 1994) utilizing $^{111}$In. Briefly, tumor cells (1-2×10[6]) were radiolabeled with 50 µCi of $^{111}$In Oxyquinoline solution (Amersham, Arlington Heights, Ill.) for 20 min at 37° C. followed by thorough washing to remove unincorporated radionuclide. Splenic lymphocytes and targets (5×10[3] cells/well) were suspended in CTL medium (complete medium with RPMI-1640:EHAA 50:50, Biowhittaker, Walkersville, Md., substituted for the RPMI-1640) and combined at effector-to-target ratios of 100:1 to 12.5:1 in 96 well U bottomed plates (Costar) and incubated for 16 hours at 37° C. with 5% $CO_2$. After incubation, supernatants were collected using a Supernatant Collection System (Skantron, Sterling, Va.) and radioactivity was quantitated using a gamma counter. (Cobra Autogamma, Packard, Downers Grove, Ill.). The percentage of specific release of $^{111}$In was determined by the standard equation: % specific lysis=[(experimental−spontaneous)/(maximum−spontaneous)]×100.

Cytotoxic T-cell Analysis: Increased CEA Specific Cytoxicity following Immunization with rV-CEA:rV-B7

Figure 7:
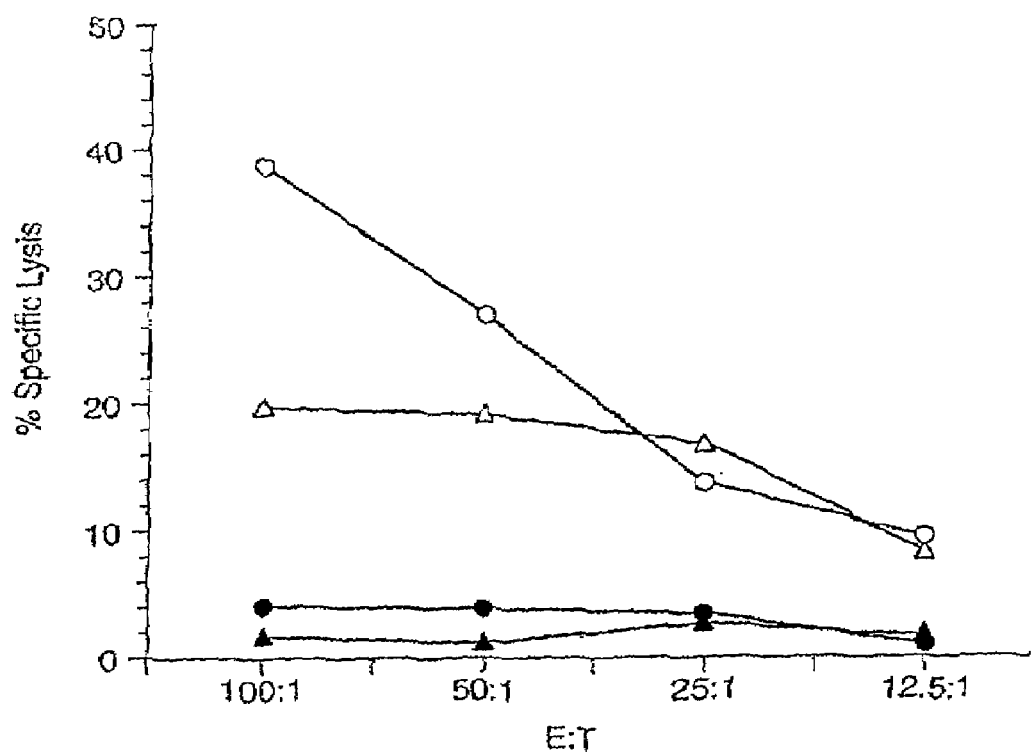
FIG. 7 shows enhancement of primary CTL activity following immunization with rV-CEA and/or rV-B7. Cytotoxic activity specific for CEA was analyzed 10 days following immunization with a total of $1 \times 10^7$ PFU of either rV-CEA: V-Wyeth (3:1; triangles) or rV-CEA:rV-B7 (3:1; circles). Splenic T-cells from each group were incubated with either MC38 cells (CEA negative; closed symbols) or MC-38-CEA-2 cells (CEA positive; open symbols) in a 16 hour cytotoxic assay. Anti-V-Wyeth CTL activity was >50% in all samples (data not shown).

To analyze the effect of the addition of rV-B7 to rV-CEA on CEA specific cytotoxic activity, splenic lymphocytes from mice immunized with the mixture of rV-B7 and rV-CEA were tested for lytic activity with murine adenocarcinoma cells that were negative for CEA (MC38) or the same cells transduced with CEA using a retroviral vector to express human CEA (MC-38-CEA-2). FIG. 7 demonstrates that T-cells from mice immunized one time with rV-CEA:V-Wyeth (3:1) did not lyse the CEA negative MC38 targets, (closed triangles), but did lyse the CEA positive MC-38-CEA-2 targets (open triangles) albeit at a low level. This CEA specific lysis was E:T ratio dependent, with lysis declining to 10% at the E:T ratio of 12.5:1. The addition of rV-B7 to the immunogen rV-CEA (rV-CEA:rV-B7; 3:1) had no effect on the lysis of MC38 cells (closed circles), but had a substantial effect on CEA specific lysis of MC-38-CEA-2 targets. Based on conversion of data to lytic units, CTL activity from mice immunized with rV-CEA:rV-B7 (3:1) exhibited a 2.8 fold increase when compared to mice immunized with rV-CEA alone.

EXAMPLE 7

Anti-Tumor Effects of rV-B7 Admixed with rV-CEA

Method

Ten C57BL/6 mice were immunized with $1\times10^7$ PFU total virus. Fourteen days following immunization, the mice were given a subcutaneous injection of $3\times10^5$ MC-38-CEA-2 cells in the right flank. Mice from the rV-CEA:rV-B7 (3:1) group remaining tumor free for at least 60 days were challenged on the opposite flank with $3\times10^5$ MC-38-CEA-2 cells. Tumors were measured by caliper in two dimensions, and the volumes calculated as previously described (Kantor, J. et al *J. Nat'l Cancer Inst.* 84:1084-1091, 1992). Animals were sacrificed in all experiments when any tumor measurement (length or width) exceeded 20 mm.

Antitumor Effects of rV-B7 Admixed with rV-CEA

Figure 8A:
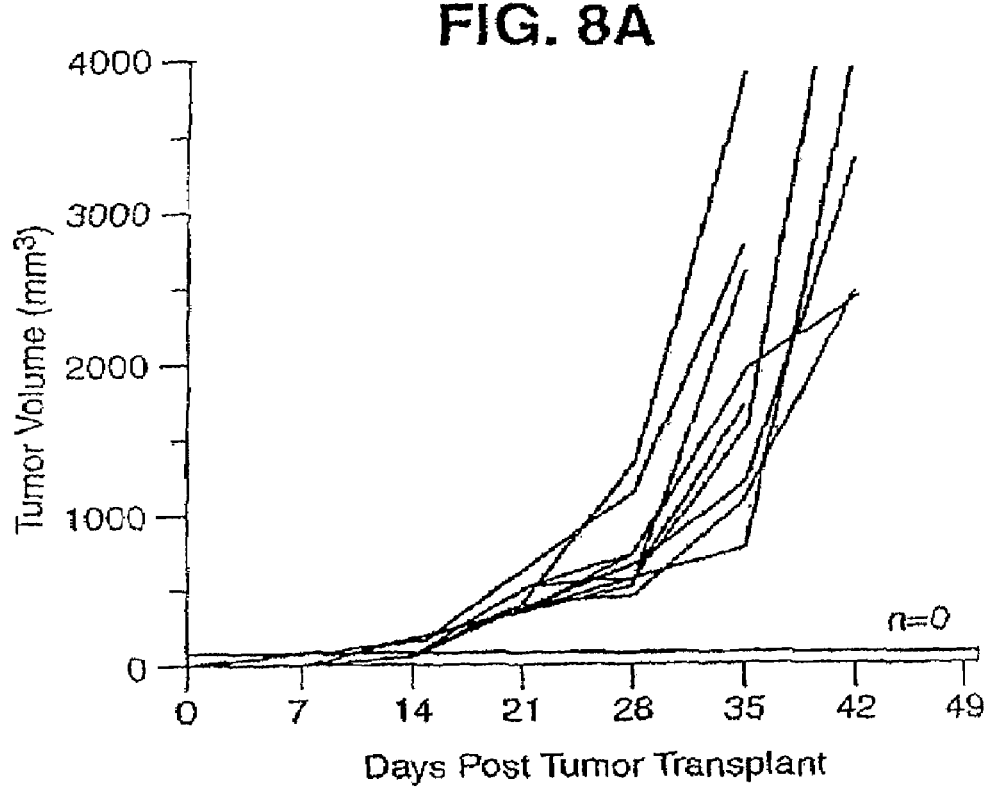
Figure 8B:
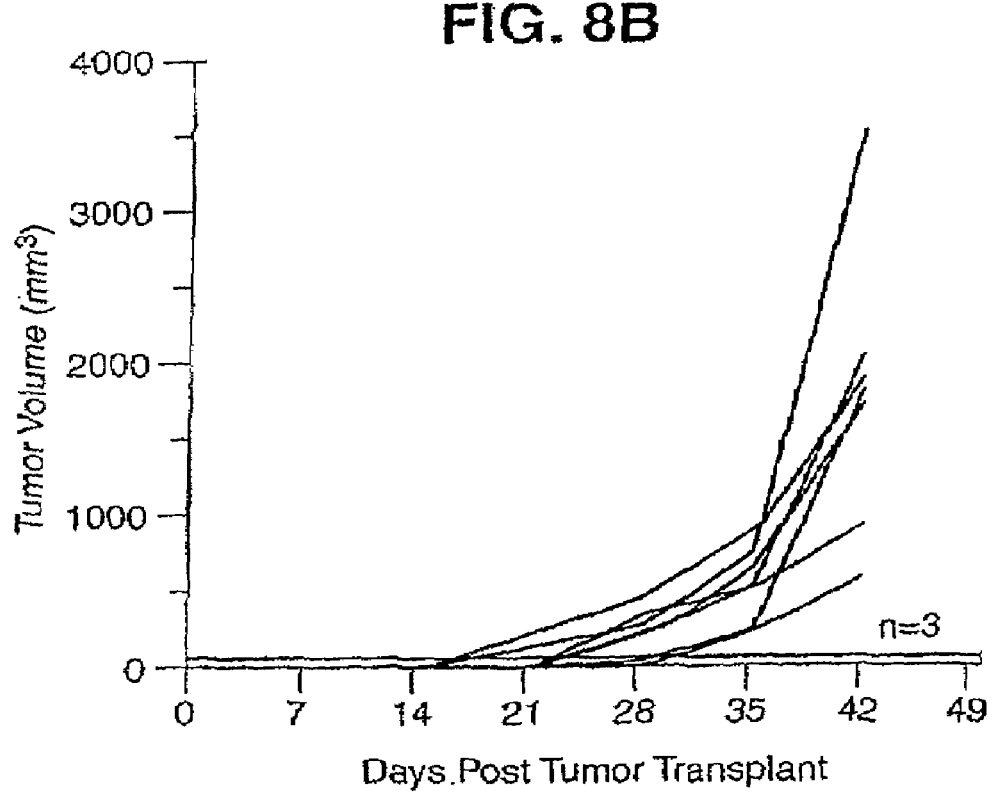

It has been previously shown that the administration of $3\times10^5$ MC-38-CEA-2 murine adenocarcinoma cells subcutaneously into syngeneic C57BL/6 mice gives rise to palpable tumors within 7-14 days followed by rapid tumor growth that is ultimately fatal (Kantor, J. et al *J. Nat'l Cancer Inst.* 84:1084-1091, 1992). It has also been shown that 3 immunizations with $1\times10^7$ PFU rV-CEA is required to protect 100% of mice from this tumor challenge (Kantor, J. et al *J. Nat'l Cancer Inst.* 84:1084-1091, 1992). To determine if immunization with the 3:1 ratio of rV-CEA and rV-B7 could protect animals from tumor challenge, we compared the growth of MC-38-CEA-2 tumor cells in C57BL/6 mice immunized only one time with a total of $10^7$ PFU of either V-Wyeth, rV-CEA:V-Wyeth (3:1); V-Wyeth:rV-B7 (3:1); or rV-CEA: rV-B7 (3:1). The injection of MC-38-CEA-2 cells (FIG. 8A) resulted in palpable tumors in all ten V-Wyeth immunized animals within 14 days. Tumor growth was progressive throughout the duration of this experiment. The injection of MC-38-CEA-2 cells into animals immunized with rV-CEA: V-Wyeth (3:1; FIG. 8B) resulted in a slight delay of onset of palpable tumor, and 70% of animals eventually became positive for tumor. The injection of MC-38-CEA-2 cells into animals immunized with Wyeth:rV-B7 (3:1; FIG. 8C) resulted in palpable tumors in 14 days with tumor growth closely resembling the V-Wyeth immunized control group (FIG. 8A). In contrast, 80% of mice immunized one time with rV-CEA:rV-B7 (3:1; FIG. 8D) failed to develop tumors. Tumor negative mice (n=8) remained tumor free for the duration of this experiment (60 days). No gross toxic effects were observed in any of these animals during the observation period. Animal weights remained within one standard deviation of normal age-matched mice. These experiments were repeated 3 additional times with similar results.

To determine if long lasting immunity to tumor cells could be induced by immunization with this combination of rV-CEA:rV-B7 (3:1), mice immunized with this ratio of recombinant viruses, which remained tumor free for at least 60 days (FIG. 8D), were then re-challenged on the opposite flank with $3\times10^5$ MC-38-CEA-2 cells (FIG. 9B). The injection of MC-38-CEA-2 cells into control naive mice (FIG. 9A) resulted in palpable tumor formation in all animals within 14 days, with progressive tumor growth throughout the duration of this experiment, whereas mice previously administered rV-CEA:rV-B7 (3:1) did not develop tumors throughout the additional 49 day observation period (FIG. 9B).

EXAMPLE 8

Construction and Characterization of rV-PSA

Recombinant Vaccinia Virus

A 786 bp DNA fragment encoding the entire open reading frame of human prostate specific antigen was amplified by reverse transcriptase PCR (GeneAmp RNA PCR Kit, Perkin Elmer, Norwalk, Conn.) from total RNA extracted from the human metastatic prostate adenocarcinoma cell line, LNCaPFGC (CRL 1740, American Type Culture Collection (ATCC), Rockville, Md.). The predicted amino acid sequence derived from the PSA coding sequence was shown to be nearly identical to the published sequence (Lundwall et al, *FEBS Letters* 214:317-322, 1987) differing only in a change from asparagine to tyrosine at position 220. The PSA DNA fragment, containing the entire coding sequence for PSA, 41 nucleotides of the 5' untranslated region, and 520 nucleotides of the 3' untranslated region, was ligated into the Xba I restriction enzyme site of the vaccinia virus transfer vector pT116. The resulting plasmid, designated pT1001, contained the PSA gene under the control of the vaccinia virus 40K promoter (Gritz et al, *J. Virology* 64:5948-5957, 1990) and the *Escherichia coli* Lac Z gene under the control of the fowlpox virus C1 promoter (Jenkins et al, *AIDS Research and Human Retroviruses* 7:991-998, 1991). The foreign genes were flanked by DNA sequences from the Hind III M region of the vaccinia genome. A plaque-purified isolate from the Wyeth (New York City Board of Health) strain of vaccinia was used as the parental virus in the construction of recombinant vaccinia virus. The generation of recombinant virus was accomplished via homologous recombination between vaccinia sequences in the Wyeth vaccinia genome and the corresponding sequences in pT1001 in vaccinia infected $RK_{13}$ cells (CCL 37, ATCC) transfected with pT1001. Recombinant clones were identified and selected by growth on $RK_{13}$ cells (CCL 37, ATCC) in the presence of 5-bromo-4-chloro-3-indoly-beta-D-galactopyranoside (X-Gal) as described previously (Panicali et al, *Gene* 47:193-199, 1986; Kaufman et al, *Int. J. Cancer* 48:900-907, 1991). Appropriate blue recombinant clones were purified by four rounds of plaque purification. Virus stocks were prepared by clarifying infected $RK_{13}$ cell lysates followed by centrifugation through a 36% sucrose cushion.

Southern Analysis of DNA Recombination

The recombinant vaccinia genome was analyzed by viral DNA extraction, restriction endonuclease digestion with Hind III and Cla I, and Southern blotting as previously described (Kaufman et al, *Int. J. Cancer* 48:900-907, 1991).

Western Analysis of PSA Protein Expression

Confluent BSC-40 cells were infected with either parental wild type vaccinia virus (designated V-Wyeth) or recombinant vaccinia-PSA (designated rV-PSA) at an MOI of 1 in Dulbecco's Modified Eagle's Medium containing 2% fetal bovine serum. After an overnight infection, the medium was removed from the cells, and an aliquot was methanol precipitated to assay for the presence of secreted PSA. The infected cells were lysed in hypotonic lysis buffer (150 mM NaCl, 0.05% EDTA, 10 mM KCl, 1 mM PMSF) and then sonicated. Cell lysates and culture media were electrophoresed on an SDS-10% acrylamide gel. The proteins were transblotted to nitrocellulose, and the blot was incubated with a rabbit antibody specific for PSA (PO798, Sigma Chemical Co., St. Louis, Mo.) for 4 hours at ambient temperature, washed, and then incubated with goat anti-rabbit phosphatase-labeled secondary antibody (AP, Kirkegaard & Perry Laboratories, Gaithersburg, Md.) and developed according to the manufacture's instructions.

Characterization of Recombinant Virus (rV-PSA)

The cDNA fragment encoding the open reading frame of human PSA was obtained by reverse transcriptase PCR using PSA specific oligonucleotide primers 5' TCTAGAAGC-CCCAAGCTTACCACCTGCA 3', 5' TCTAGAT-CAGGGGTTGGCCACGATGGTGTCCTTGATCCACT 3', and ligated into vaccinia virus transfer vector pT116. This vector contains a strong vaccinia virus early/late promoter (designated 40K) upstream of the multiple cloning site to drive the synthesis of the inserted gene product. The ligation and orientation of the PSA DNA fragment, as well as promoter position were verified by PCR and sequencing. The chimeric vector construct was inserted into the vaccinia virus genome Hind III M site by homologous recombination as previously reported (Kaufman et al, *Int. J. Cancer,* 48:900-907, 1991) and confirmed by Southern analysis probing with $^{32}$P radiolabeled DNA corresponding to PSA sequences and vaccinia sequences in the Hind III M region (data not shown).

Expression of recombinant PSA protein was confirmed by western blot analysis of supernatant fluids and protein extracts from rV-PSA infected BSC 40 cells. These cells are routinely used for the evaluation of recombinant vaccinia products (Earl et al, *Current Protocols in Molecular Biol.,* 2.16.15.1-16.18.9, 1993). Incubation of cell supernatant blots from rV-PSA infected cells with rabbit anti-PSA antibody revealed a single immunoreactive polypeptide of approximately 33,000 daltons (data not shown). Similarly, incubation of protein extract blots from rV-PSA infected cells revealed a single band of the same molecular weight (data not shown). This is consistent with the predicted size of the PSA molecule (Armbruster et al, *Clin. Chem.* 39:181-195, 1993; Wang et al *Methods in Cancer Research,* 19:179-197, 1982). Cell supernatant blots or protein extract blots from cells infected with parental strain V-Wyeth remained negative for expression of PSA. These results thus demonstrate that a recombinant vaccinia virus can faithfully express the human PSA gene product.

EXAMPLE 9

Increased PSA Specific Cytotoxicity following Immunization with rV-PSA:rV-B7

Cell Lines

MC-38, a murine colonic adenocarcinoma cell line (Fox, B. A. et al *J. Biol. Response Mod.* 9:499-511, 1990) was obtained from Dr. Bernard Fox (National Cancer Institute, National Institutes of Health, Bethesda, Md.). The LNCaP human prostate adenocarcinoma cell line (Horoszewicz, J. S. et al In: Murphy, G. P. (ed.) Models for Prostate Cancer, pp. 115-132, New York: A. R. Liss, 1980) was obtained from the American Type Culture Collection (Rockville, Md.). The Moloney murine sarcoma virus retroviral vector pLNSC (Miller, A. D. et al *Biotechniques* 7:980-990, 1989) was obtained from Dr. A. Dusty Miller (Fred Hutchinson Cancer Research Center, Seattle, Wash.). The murine ecotropic packaging cell line GP+E-86 (Hesdorffer, C. *Hematol. Oncol. Clin. North Am.* 5(3):423-432, 1991), MC-38, PSA/MC-38 and pLNSX/MC-38 were maintained in Dulbecco's modified Eagle medium (DMEM) (Gibco BRL, Gaithersburg, Md.) with 10% fetal bovine serum (FBS) (Gibco BRL). PSA/MC-38 and pLNSX/MC-38 cell lines were kept tinder continuous selective pressure in 1 mg G418 sulfate/ml (Gibco BRL). LNCaP was maintained in RPMI-1640 medium (Gibco BRL) containing 10% FBS.

Cloning of PSA cDNA

Complementary DNA (cDNA) was synthesized from total RNA from the human prostate adenocarcinoma cell line LNCaP using the GeneAmp RNA polymerase chain reaction (PCR) Kit (Perkin Elmer Corp., Norwalk, Conn.). Human PSA-specific oligonucleotide primers were selected based on the human mRNA sequence (GenBank accession number X07730) using the MacVector 4.1.4. computer program (Kodak Co., Rochester, N.Y.). The 5'(5' AGA GAG AGC CTC AAG CTT CAG CCC CAA GCT TAC CAC CTG CA 3') and 3'(5' AGA GAG AGC AAG CTT AGT CCC TCT CCT TAC TTC AT 3') primers, containing HindIII restriction enzyme sites, were used to synthesize full-length PSA cDNA by PCR. The 1.5-kb PSA gene was ligated to HindIII restriction endonuclease-digested pLNSX DNA and was used to transform competent CH5α *Escherichia coli* cells (Gibco BRL). Ampicillin-resistant colonies were tested for orientation of the cDNA insert by PCR using a vector-specific 5' oligonucleotide primer (5' TTT GGA GGC CTA GGC TTT TGC AAA 3') and the PSA-specific 3' primer described above. Transformants were selected with PSA cDNA in the sense orientation, characterized by restriction endonuclease digestion, and sequenced by the dideoxy method using Sequenase (United States Biochemical Corp., Cleveland, Ohio). Sequence analysis of the gene recovered by PCR confirmed that the gene was identical to the human PSA gene sequence in GenBank.

Transfection and Transduction of DNA into Target Cells, MC-38

The PSA/pLNSX plasmid (5 μg) was transfected into MC-38 cells using Transfection-reagent (DOTAP) (Boehringer Mannheim Biochemica, Indianapolis, Ind.) according to the manufacturer's instructions. At 24 h, selection medium containing 100 μg/ml (wt/vol) of G418 was added to the cells. Selective pressure was maintained by continuous culture in DMEM containing 10% PBS and increasing concentrations of G418 (to 1 mg/ml). Drug-resistant cells were cloned by limiting dilution. Conditioned medium from the cloning walls was tested using the solid phase, double-determinant Tandem-R PSA immunoradiometric assay (Hybritech Inc., San Diego, Calif.). The highest producers of secreted PSA were cloned twice by limiting dilution. One clone, designated PSA/MC-38, produced approximately 10 ng PSA/ml.

Vector-transduced, PSA-negative MC-38 cells were developed as follows. GP+E+86 cells, an ecotropic murine packaging cell line, were transfected with 2 μg of pLNSX vector DNA using DOTAP transfection-reagent, as described above. At 24 h the transfected cells were replated and grown in selection medium (1.0 mg G418/ml). Cells surviving G418 selection and containing pLNSX were grown in medium without G418, and this medium was added to MC-38 cells in the presence of 8 μg/ml of polybrene (Sigma Chemical Co., St. Louis, Mo.). The transduced MC-38 cells were grown in the presence of G418 for 3 weeks. Individual drug-resistant colonies were isolated by sterile cloning rings and characterized by PCR for the presence of pLNSX. One clone, pLNSX/MC-38, was used for further study.

Cytolytic Response Methods

Mice were immunized with rV-PSA using the basic protocol as described in Example 6. The source of rV-PSA, made as described in Example 8, was Therion Biologics Corporation, Cambridge, Mass. The MC38 murine colonic adenocarcinoma cell line expressing human PSA (MC38-PSA) as described above and in Karr, J. F. et al (*Cancer Research*, in press) was used as the antigen specific target.

Cytotoxic T-cell Analysis: Increased PSA Specific Cytotoxicity following Immunization with rV-PSA:rV-B7

Figure 10:
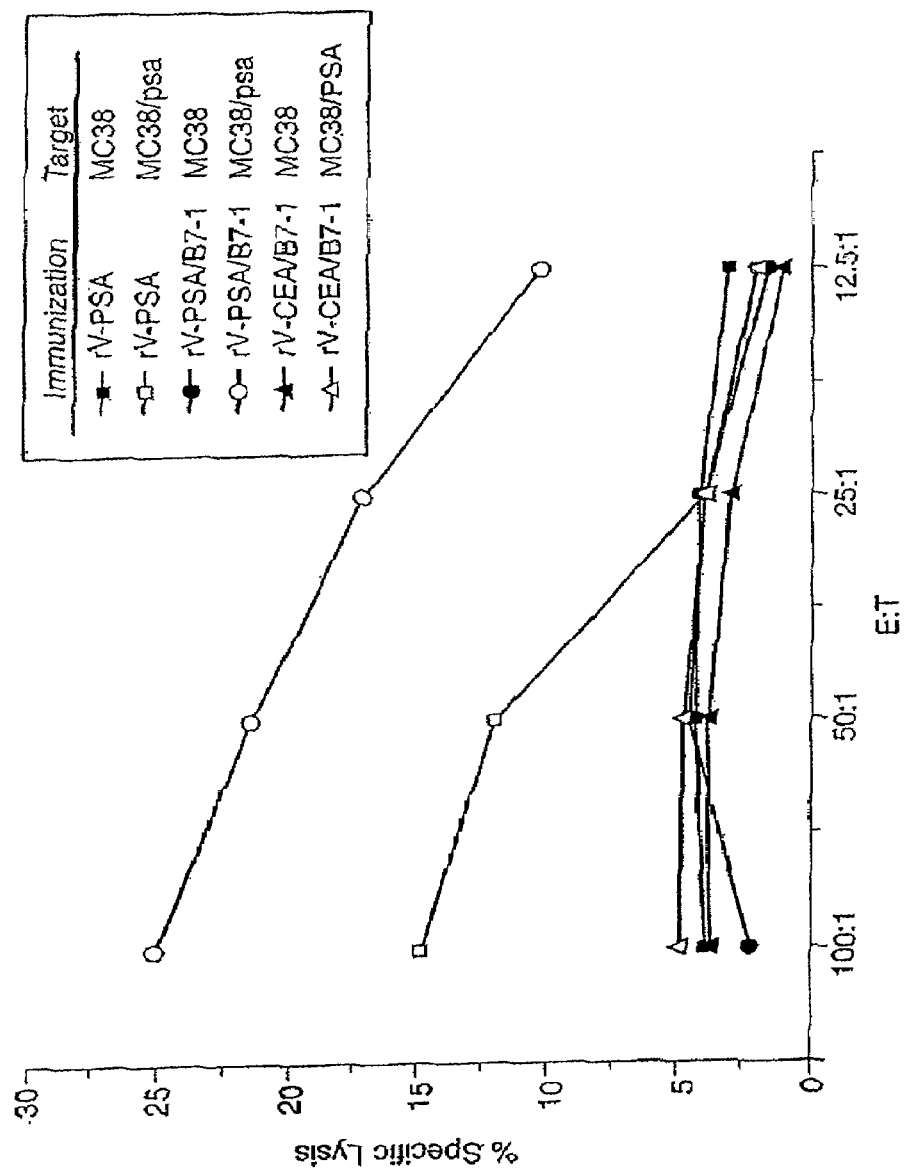
FIG. 10 shows enhancement of primary CTL activity following immunization with rV-PSA and rV-B7-1. Cytotoxic activity specific for PSA was analyzed 10 days following immunization with a total of $1\times10^7$ PFU of rV-PSA, rV-PSA: rV-B7-1 or rV-CEA:r-B7-1. Splenic T-cells from each group were incubated with either MC38 cells or MC38-PSA cells in a 16 hour cytotoxic assay.

To analyze the effect of the addition of rV-B7 to rV-PSA on PSA specific cytotoxic activity, splenic lymphocytes from mice immunized with the mixture of rV-B7 and rV-PSA were tested for lytic activity with murine adenocarcinoma cells that were negative for PSA (MC38) or the same cells transduced with PSA (MC38-PSA). FIG. 10 demonstrates that T-cells from mice immunized one time with rV-PSA did not lyse PSA negative MC38 targets, but did lyse the PSA positive MC38-PSA targets. The addition of rV-B7 to the immunogen rV-PSA had no effect on the lysis of MC38 cells but had a substantial effect on PSA specific lysis of MC38-PSA targets (FIG. 10). The specificity of the lysis was further demonstrated as T-cell from mice immunized with a different antigen, rV-CEA:B7-1 did not lyse MC38-PSA targets.

EXAMPLE 10

Use of Lymphocytes Sensitized to Immunogenic Peptides Derived from CEA Antigens for Therapeutically Treating Mammals Afflicted with Cancer T-lymphocytes presensitized to the CEA antigen may be effective in therapeutically treating mammals afflicted with cancer. T-lymphocytes from peripheral blood or tumor suspensions and cultured in vitro (Kawakami, Y. et al. (1988) *J. Exp. Med.* 168:2183-2191). The T-lymphocytes are exposed to cells infected with the recombinant virus expressing a CEA associated antigen and/or recombinant virus expressing B7.1 and/or B7.2 for a period of about to 1-16 hours at a concentration of 1-10 MOI. T-lymphocytes exposed to the antigen will be administered to the mammal, preferably a human at about $10^7$-$10^{12}$ lymphocytes. The lymphocytes may be administered either intravenously, intraperitoneally or intralesionally. This treatment may be administered concurrently with other therapeutic treatments such as cytokines, radiotherapy, surgical excision of tumor lesions and chemotherapeutic drugs, adoptive T lymphocyte therapy.

While the invention is described above in relation to certain specific embodiments, it will be understood that many variations are possible, and that alternative materials and reagents can be used without departing from the invention. In some cases such variations and substitutions may require some experimentation, but will only involve routine testing.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments.

All references and patents referred to are incorporated herein by reference.

What is claimed is:

1. A composition comprising (a) a first recombinant poxvirus encoding granulocyte-monocyte-colony stimulating factor (GM-CSF) and (b) a second recombinant poxvirus encoding an antigen or immunological epitope thereof.

2. The composition of claim 1, further comprising at least one immunostimulatory molecule selected from the group consisting of B7.1, B7.2, ICAM-1, and LFA-3.

3. The composition of claim 2, wherein the at least one immunostimulatory molecule is encoded by the first or second recombinant poxvirus.

4. The composition of claim 2, wherein the first and second recombinant poxvirus are selected from the group consisting of vaccinia, MVA, canarypox, and fowlpox.

5. A method of enhancing an immune response in a mammal comprising administering the composition of claim 1 to the mammal, thereby enhancing the immune response in the mammal.

6. The method of claim 5, wherein the composition further comprises at least one immunostimulatory molecule selected from the group consisting of B7.1, B7.2, ICAM-1, and LFA-3.

7. The method of claim 6, wherein the at least one immunostimulatory molecule is encoded by the first or second recombinant poxvirus.

8. The method of claim 5, wherein the first and second recombinant poxvirus are selected from the group consisting of vaccinia, MVA, canarypox, and fowlpox.

* * * * *

SEQUENCE LISTING

<160> NUMBER OF SEQ ID NOS: 9

<210> SEQ ID NO 1
<211> LENGTH: 27
<212> TYPE: DNA
<213> ORGANISM: Artificial Sequence
<220> FEATURE:
<223> OTHER INFORMATION: Synthetic

<400> SEQUENCE: 1
ggtaccatgg cttgcaattg tcagttg    27

<210> SEQ ID NO 2
<211> LENGTH: 24
<212> TYPE: DNA
<213> ORGANISM: Artificial Sequence
<220> FEATURE:
<223> OTHER INFORMATION: Synthetic

<400> SEQUENCE: 2
ctcgagctaa aggaagacgg tctg                                          24

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3
ggtaccgaag cacccacgat ggac                                          24

<210> SEQ ID NO 4
<211> LENGTH: 27
<212> TYPE: DNA
<213> ORGANISM: Artificial Sequence
<220> FEATURE:
<223> OTHER INFORMATION: Synthetic

<400> SEQUENCE: 4
ctcgagtcac tctgcatttg gttttgc                                       27

<210> SEQ ID NO 5
<211> LENGTH: 28
<212> TYPE: DNA
<213> ORGANISM: Artificial Sequence
<220> FEATURE:
<223> OTHER INFORMATION: Synthetic

<400> SEQUENCE: 5
tctagaagcc ccaagcttac cacctgca                                      28

<210> SEQ ID NO 6
<211> LENGTH: 41
<212> TYPE: DNA
<213> ORGANISM: Artificial Sequence
<220> FEATURE:
<223> OTHER INFORMATION: Synthetic

<400> SEQUENCE: 6
tctagatcag gggttggcca cgatggtgtc cttgatccac t                       41

<210> SEQ ID NO 7
<211> LENGTH: 41
<212> TYPE: DNA
<213> ORGANISM: Artificial Sequence
<220> FEATURE:
<223> OTHER INFORMATION: Synthetic

<400> SEQUENCE: 7
agagagagcc tcaagcttca gccccaagct taccacctgc a                       41

<210> SEQ ID NO 8
<211> LENGTH: 35
<212> TYPE: DNA
<213> ORGANISM: Artificial Sequence
<220> FEATURE:
<223> OTHER INFORMATION: Synthetic

<400> SEQUENCE: 8
agagagagca agcttagtcc ctctccttac ttcat                              35

<210> SEQ ID NO 9
<211> LENGTH: 24
<212> TYPE: DNA

```
<213> ORGANISM: Artificial Sequence
<220> FEATURE:
<223> OTHER INFORMATION: Synthetic

<400> SEQUENCE: 9
tttggaggcc taggcttttg caaa                                              24
```